United States Patent
Lihme et al.

(10) Patent No.: US 9,220,997 B2
(45) Date of Patent: Dec. 29, 2015

(54) EXPANDED BED COLUMN AND DISPOSABLE CHROMATOGRAPHY

(75) Inventors: Allan Lihme, Birkerød (DK); René Oehlenschläger Holte, Søborg (DK); Kurt Hauge Jensen, Roskilde (DK); Tony Christensen, Store Fuglede (DK)

(73) Assignee: DPX HOLDINGS B.V., Amsterdam (NL)

( * ) Notice: Subject to any disclaimer, the term of this patent is extended or adjusted under 35 U.S.C. 154(b) by 708 days.

(21) Appl. No.: 12/532,806

(22) PCT Filed: Mar. 28, 2008

(86) PCT No.: PCT/EP2008/053732
§ 371 (c)(1),
(2), (4) Date: Dec. 21, 2009

(87) PCT Pub. No.: WO2008/116935
PCT Pub. Date: Oct. 2, 2008

(65) Prior Publication Data
US 2010/0084344 A1    Apr. 8, 2010

Related U.S. Application Data

(60) Provisional application No. 60/908,564, filed on Mar. 28, 2007.

(51) Int. Cl.
*B01D 15/18*    (2006.01)
*C07K 1/22*    (2006.01)
*G01N 30/38*    (2006.01)

(52) U.S. Cl.
CPC ........... *B01D 15/1807* (2013.01); *C07K 1/22* (2013.01); *G01N 30/38* (2013.01)

(58) Field of Classification Search
CPC ....... B01D 15/1807; G01N 30/38; C07K 1/22

USPC ................... 210/635, 656, 659, 198.2, 502.1
See application file for complete search history.

(56) References Cited

U.S. PATENT DOCUMENTS 4,648,969 A * 3/1987 Swanson ................. 210/237
5,167,809 A * 12/1992 Mann et al. ................ 210/198.2
(Continued)

FOREIGN PATENT DOCUMENTS

EP    0 005 650 A1    5/1979
EP    0 922 489 A2    6/1999
(Continued)

OTHER PUBLICATIONS

"Moving Chromatography Up Front in a Downstream Process", http://www.upfront-dk.com/technology Downloaded on Aug. 16, 2006, 2 pgs.
(Continued)

*Primary Examiner* — Ernest G Therkorn
(74) *Attorney, Agent, or Firm* — Pierce Atwood LLP; Raymond G. Arner, Esq.

(57) ABSTRACT

In the field of expanded bed adsorption chromatography, with particular but not exclusive relevance to disposable expanded bed chromatography columns, a method of conducting upward flow expanded bed chromatography comprising: supplying a liquid via an inlet to a stationary phase medium contained in a column, allowing adsorption of at least one component from the liquid by the stationary phase medium, withdrawing the liquid from the column via an outlet, regulating the expansion of the stationary phase medium by regulation of the flow rate of the liquid through at least the inlet, and restricting any overpressure in the headspace of the column to not more than the outside pressure plus 0.1 bar, is provided. In addition, apparatus for use in said method, in particular columns for use in expanded bed chromatography, are provided.

21 Claims, 17 Drawing Sheets

(56) References Cited

U.S. PATENT DOCUMENTS

| | | | |
|---|---|---|---|
| 5,522,993 | A | 6/1996 | Carlsson et al. |
| 5,759,395 | A | 6/1998 | Hagerlid |
| 5,837,826 | A * | 11/1998 | Flickinger et al. ............ 530/413 |
| 6,027,650 | A * | 2/2000 | Van Reis et al. ............... 210/656 |
| 6,039,866 | A * | 3/2000 | Tanaka et al. .................. 210/136 |
| 6,498,236 | B1 | 12/2002 | Lihme et al. |
| 6,620,326 | B1 * | 9/2003 | Lihme et al. ................... 210/635 |
| 6,623,630 | B1 | 9/2003 | Staffler |
| 6,706,191 | B1 * | 3/2004 | Leijon ............................ 210/656 |
| 6,783,962 | B1 * | 8/2004 | Olander et al. ............... 435/91.1 |
| 7,279,094 | B2 | 10/2007 | Hofmann |
| 7,682,510 | B2 * | 3/2010 | Berglof et al. ................. 210/635 |
| 8,309,709 | B2 | 11/2012 | Berg et al. |
| 2004/0048357 | A1 | 3/2004 | Hubbuch et al. |
| 2007/0193954 | A1 * | 8/2007 | Busson .......................... 210/656 |
| 2007/0199899 | A1 * | 8/2007 | Alaska ........................... 210/659 |
| 2009/0325427 | A1 | 12/2009 | Philipp |
| 2010/0084344 | A1 * | 4/2010 | Lihme et al. ................... 210/656 |
| 2012/0225618 | A1 | 9/2012 | Nouchi |

FOREIGN PATENT DOCUMENTS

| | | |
|---|---|---|
| GB | 1 411 346 | 7/1972 |
| JP | 2004212190 A | 7/2004 |
| JP | 2006174610 A | 6/2006 |
| WO | WO 90/14157 | 11/1990 |
| WO | WO 92/00799 | 1/1992 |
| WO | WO 97/10887 | 3/1997 |
| WO | WO 98/08603 | 3/1998 |
| WO | WO 99/65586 | 12/1999 |
| WO | WO 00/25883 | 5/2000 |
| WO | WO 00/57982 | 10/2000 |
| WO | WO 01/58924 A2 | 8/2001 |
| WO | WO 01/85329 A2 | 11/2001 |
| WO | WO 03/024588 A1 | 3/2003 |
| WO | WO 2004/008138 A2 | 1/2004 |
| WO | WO 2004/082397 A1 | 9/2004 |
| WO | WO 2005/082483 A1 | 9/2005 |
| WO | WO 2005/082926 A1 | 9/2005 |
| WO | WO 2006/001867 A2 | 1/2006 |

OTHER PUBLICATIONS

"FastLine EPA Absorbents", http://www.upfront-dk.com/composite-13.htm Downloaded on Aug. 16, 2006, 1 pg.

"FastLine EBA Columns", http://www.upfront-dk.com/composite-14.htm Downloaded on Aug. 16, 2006, 2 pgs.

"Mixed Mode Ligand Chemistry", http://www.upfront-dk.com/composite-15.htm Downloaded on Aug. 16, 2006, 1 pg.

Rolf Hjorth, "Expanded—bed adsorption in industrial bioprocessing: recent developments", Journal of Bioseparation (1997) pp. 230-235.

Japanese Office Action "Notice of Reasons for Rejections," dated Jun. 11, 2013, Patent Application No: P2010-500292, 6 pages.

Japanese Final Office Action "Notice of Reasons for Rejections," dated May 26, 2015, Patent Application No: P2013-256280, 4 pages.

Japanese Final Office Action "Decision to Decline the Amendment," dated May 26, 2015, Patent Application No: P2010-500292, 4 pages.

\* cited by examiner

EXPANDED BED COLUMN AND DISPOSABLE CHROMATOGRAPHY

CROSS-REFERENCE TO RELATED PATENT APPLICATIONS

This application is the U.S. National Phase of PCT/EP2008/053732 filed Mar. 28, 2008, which claims priority to U.S. Provisional Application No. 60/908,564 filed Mar. 28, 2007, which is incorporated herein by reference in it's entirety.

The present invention relates to expanded bed adsorption (EBA) systems. It has particular but not exclusive relevance to disposable expanded bed chromatography columns.

The purification of fermentation broths in order to extract biopharmaceuticals therefrom is a developing field. In particular, the purification of monoclonal antibodies is of increasing importance due to their investigation as therapeutic and diagnostic agents.

Monoclonal antibodies are usually produced, usually in murine, human or humanised form, from a hybridoma fermentation broth or a microbial fermentation broth. Traditionally, the broth would be purified by a selective reversible precipitation process that aimed to precipitate the desired immunoglobulins while leaving other proteins in solution. However, this process is time consuming, produces antibodies of low purity, and creates a problem of disposal of the supernatant containing the unwanted proteins and precipitation agents. As a result, the use of chromatography to purify the fermentation broth has been developed.

Chromatography requires the use of a mutually immiscible mobile phase and stationary phase, each having different affinities for the components of the mixture to be separated. The relative affinity of each component of the mixture to be purified for the two phases determines the rate of migration of that component through the stationary phase in the direction of flow of the mobile phase. Careful selection of the mobile and stationary phases may allow the separation of components in the mixture by ensuring that the rates of migration of the components are sufficiently different to permit each component of interest to elute separately from the stationary phase. The stationary phase may be a support matrix to which a ligand bearing functional groups capable of binding to the component(s) of interest may be attached. There are two broad general methods of carrying out chromatography: using a packed bed of the stationary phase through which the mobile phase is forced by use of applied pressure; or expanded bed adsorption, in which the pressure applied to the mobile phase is at least much reduced and the density of the stationary phase is selected to create a stable fluidised bed in a certain range of flow rate of the mobile phase.

For the isolation of monoclonal antibodies, the most widely used method of chromatography is Protein A affinity chromatography. This may be used in conjunction with hydrophobic interaction chromatography (HIC) which requires the addition of a lyotropic salt to the fermentation broth in order that the hydrophobic matrix (stationary phase) binds the antibody efficiently, followed by the use of a decreasing concentration of lyotropic salt solution in order to elute the antibody from the solid phase. The use of the lyotropic salt causes problems of disposal of the waste products, especially as the presence of the salt may prevent the use of the antibody-depleted raw material. Alternatively, or additionally, ion exchange chromatography may be used as an additional purification step.

Protein A chromatography may be carried out on packed-bed Protein A Sepharose columns. The stationary phase of these columns is re-usable up to twenty or more times, and must be cleaned using sodium hydroxide solution followed by verification of the cleanliness of the column before re-use. This is time consuming and requires significant down-time of the purification apparatus. Furthermore, Protein A is unstable at pH values above pH 12 and each cleaning cycle using sodium hydroxide therefore shortens the operational life time of the adsorbent. The packed-bed method of elution requires that the apparatus containing the column be capable of withstanding the back pressure applied to create the required flow of the mobile phase through the column. This generally requires a permanent installation to contain the stationary phase. Columns are typically of stainless steel or heavy duty glass, chosen for strength and for resistance to the required conditions for repeated cleaning of the stationary phase and column. These columns are not disposed of but re-used many times. Particulates, such as cells and cell debris, in the mixture to be purified must be removed from the mixture before introduction to the column to avoid clogging of the stationary phase. Clarification procedures such as filtration and centrifugation are expensive, time consuming and lead to a significant loss of product. Further, the Protein A ligand itself is expensive.

There have therefore been efforts to provide a cheaper and more efficient method of purification of antibodies and of fermentation broths in general.

Alternative stationary phases to the Protein A stationary phase have been proposed. MBI Hypercel® is a commercially-available adsorbent comprising mercapto-benzimidazole-sulphonic acid ligands stated to provide both hydrophobic interactions and ionic interactions with antibodies. U.S. Pat. No. 6,498,236 describes a method of purification of antibodies using ligands of the formula M-SP1-X-A-SP2-Acid, wherein: M=matrix backbone; SP1=spacer; X=O, S, or NH; A=a mono- or bicyclic optionally substituted aromatic or heteroaromatic moiety; SP2=optional spacer; Acid=an acidic group. WO97/10887 discloses hydrophobic ligands of increased selectivity for proteinaceous materials, wherein the structure of the ligand comprises a heteroaromatic entity with at least one ring-forming atom is nitrogen. WO03/024588 discloses a multimodal ligand capable of both hydrophobic and ionic interaction.

The use of expanded bed adsorption in place of the commonly-used packed bed columns has been disclosed. Expanded bed adsorption may be performed using an upward flow of the mobile phase through the stationary phase, in which case it is required that the stationary phase is denser than the mobile phase in order to form a stable fluidised bed, or a downward flow of the mobile phase, in which case the stationary phase should be less dense than the mobile phase for formation of a stable fluidised bed. The stationary phase should adsorb the compound(s) of interest from the mixture, allowing unwanted compounds to be washed away using a mobile phase having low affinity for the compound(s) of interest, and then the compound(s) of interest may be eluted from the column using an eluent having a high affinity for that (those) compound(s). The elution may take place using a fluidised bed or may take place in packed bed mode by applying pressure to the eluent. The maximum flow of mobile phase through an expanded bed stationary phase is determined by the density and diameter of the particles used in order that the stationary phase forms a stable expanded bed. Particles of stationary phase medium having a controlled density and diameter for use in expanded bed adsorption systems may be made using a porous composite material whose pore size, particle size and density may be selected, and which may be coated if desired with a coating having affinity for the compound to be purified using the stationary phase. Examples of such media are the Streamline matrix of Pharmacia Biotech, Sweden, and the UpFront Matrix of UpFront Chromatography A/S, Denmark, both of which consist of one or more particles inside an agarose sphere. WO00/57982 discloses a stationary phase for use in expanded bed adsorption in which the density of the particles is at least 2.5 gml$^{-1}$ and the average particle diameter is 5-75 µm, and the core of the particles is a non-porous material having a density of at least 3.0 gml$^{-1}$. Suitable core materials include steel beads. The coating of the core may be a polymer base matrix bearing either chargeable groups or affinity ligands.

Introduction of the mixture to be purified and the mobile phase to the stationary phase of the column while allowing the stable formation of a fluidised bed is a problem that has been addressed in the prior art. It is known that the formation of channels in the stationary phase due to the introduction of the mixture and/or mobile phase causes a reduction in the stability of the expansion of the bed (due to, for example, backmixing and unwanted turbulence), and decreases the efficacy of the separation. This problem increases with the diameter of the column to be used, and is therefore particularly acute in columns intended for purification on a commercial scale. WO99/65586 and WO01/85329 seek to solve this problem by providing a rotating distributor where the mixture and/or mobile phase is introduced to the column. In WO01/85329, the distributor comprises a plurality of outlets through which liquid may pass to reach the column. In the case of an upflow column, the distributor is provided at the base of the column, and the outlets are preferably directed towards the bottom of the column (i.e. the opposite direction to the direction of movement of the mobile phase) in order to minimise turbulence in the stationary phase resulting from the liquid streams entering the column. The distributor is rotated sufficiently quickly to ensure even distribution of the liquid across the bottom of the column, but sufficiently slowly to minimise the "stirring zone" formed in the stationary phase in which stable expansion cannot be achieved. It is shown in the Examples that use of a non-rotating distributor leads to the formation of channels in the stationary phase, and thus to a less stable expanded bed. In WO99/65586, the distribution of fluid is achieved by using magnetic stirring of the stationary phase at the bottom of the column. Again, it is preferred to minimise the height of the stirring zone.

The problem of clogging of parts of the column by particulates and insolubles in the mixture to be purified has been addressed in the prior art. In WO2006/001867, the system developed by Pharmacia and sold under the trade mark Streamline is discussed. It is stated that the inclusion of a screen having a pore size of around 20 µm between the flow distributor plate and the stationary phase medium at the bottom of the column will prevent the stationary phase medium from passing through the screen into the flow distributor plate, while allowing passage of cells and cell debris. The application states that such an arrangement does not prevent the formation of clumps of particulates that form a viscous layer known as a "cake" blocking the pores of the inlet screen. The solution to this problem proposed by WO2006/001867 is to use an inlet and outlet at the bottom of the column below the inlet screen so that the fluid flow can be circulated in a stream passing across the bottom of the inlet screen to wash away the "cake". Alternatively, the use of pulsed flows or vibration of the column is proposed to dislodge blockages from the inlet screen.

As stated above, the necessity to clean and verify the cleanliness of the widely-used Protein A columns has the disadvantage of being time-consuming, resulting in a significant time period during which the purification apparatus cannot be used. The overall process for production of antibodies involves a fermentation step, which may be carried out in a single use rocking tank, clarification by means of filtration on single-use filters, followed by the chromatography step capturing the product as described above, and optionally one or several chromatographic polishing steps to remove impurities, followed by membrane filtration of the purified product carried out using disposable membranes. It is therefore apparent that the only stage of the operation not carried out using single-use disposable apparatus is/are the chromatography step(s). WO99/65586 discloses the desirability of providing a disposable version of the columns described therein. These columns include mechanically-driven stirrer blades or magnetic stirrer bars.

The inventors have realised that the use of a disposable column would allow the supply of sterile columns that could be exchanged after use with minimal down-time of the system. However, the usual manner of driving the mobile phase through the column using a single pump situated upstream of the inlet creates a pressure in the headspace of the column (i.e. the space in the column above the mobile phase and below the top) that is necessary to drive the mobile phase through the outlet after passing thorough the stationary phase medium, and thus the columns described in WO99/65586 must be capable of safely withstanding such pressure. In addition to the pressure created to drive the mobile phase through the outlet, the column needs to be pressure rated to the maximum pressure delivered by the inlet pump in order to safeguard against any unintended blocking of the outlet (e.g. a closed valve) while the inlet pump is still running. Such columns would be expensive to construct and heavy to transport, thus making them poorly adapted for disposable use due to the high cost to the user. An air vent that does not eliminate the need for pressure rating of the column is disclosed as an optional feature of the columns in WO99/65586, and is used: (a) to provide a negative pressure in the headspace while establishing a stable expanded bed, in order that the stationary phase is allowed to expand and the mobile phase does not leave through the outlet; and (b) to provide a positive pressure to the headspace in order to assist the mobile phase in leaving through the outlet during the adsorption phase after a stable expanded bed is formed. It is clear, then, that the columns in WO99/65586 must be able to withstand the negative and positive pressures applied to the headspace, even if it is intended that they are used for expanded bed elution rather than packed bed elution.

The inventors have realised that if an expanded bed adsorption system requiring minimal back-pressure is used in the chromatography step, then it is not necessary to install containment for pressurised equipment, and the column may be made of a light, disposable material which need not be capable of withstanding elevated pressures.

Accordingly, in a first aspect, the present invention provides a method of conducting upward flow expanded bed adsorption chromatography of a liquid comprising at least one component to be separated therefrom, comprising:
supplying the liquid via an inlet to a stationary phase medium contained in a column, resulting in expansion of the stationary phase medium below a variable volume of headspace;
allowing adsorption of the at least one component from the liquid by the stationary phase medium;
withdrawing the liquid from the column via an outlet;
regulating the expansion of the stationary phase medium by regulation of the flow rate of the liquid through at least the inlet; and restricting any overpressure in the headspace with respect to the pressure outside the column to be not more than said outside pressure plus 0.1 bar.

Preferably, the overpressure is not more than 0.08 bar, more preferably not more than 0.05 bar, such as 0.01 bar, or 0.005 bar.

In a second aspect, the present invention provides an apparatus to be used in conjunction with the method of the first aspect.

In a third aspect, the present invention provides a column for use in conjunction with the method of the first aspect and/or the apparatus of the second aspect. The column according to this aspect comprises: a lower portion comprising an inlet for the passage of liquid into the column; an upper portion comprising an outlet for said liquid; and a stationary phase medium contained in the column; wherein the upper portion of the column further comprises a vent providing a fluid connection between the interior and the exterior of the column.

In a fourth aspect, the present invention provides a column for use in expanded bed chromatography, comprising: a lower portion comprising an inlet for the passage of liquid into the column; an upper portion comprising an outlet for said liquid; and a stationary phase medium contained in the column; wherein the inlet is not adapted for driven stirring of the stationary phase medium.

In a fifth aspect, the present invention provides an apparatus for conducting expanded bed chromatography, comprising the column of the fourth aspect of the invention. Preferably, said apparatus further comprises at least a first pump upstream of the inlet of the column and a second pumps downstream of the outlet of the column.

In a sixth aspect, the present invention provides a method of conducting expanded bed chromatography of a liquid comprising at least one component to be separated therefrom, comprising:
supplying the liquid via an inlet by means of at least a first pump upstream of the inlet to a stationary phase medium contained in a column, resulting in expansion of the stationary phase medium below a variable volume of headspace;
allowing adsorption of the at least one component from the liquid by the stationary phase medium; and
withdrawing the liquid from the column via an outlet by means of at least a second pump downstream of the outlet.

Preferably, the method is conducted using a column according to the fourth aspect of the invention.

The preferred features stated below may apply to all aspects of the invention to which they are appropriate, and may be combined in any appropriate fashion.

Suitably, the vent may comprise a protective filter, suitably a microfilter, and said filter may prevent contaminants from entering the column, and/or may prevent microorganisms from either leaving or entering the column.

Preferably, the vent is a simple opening in the column. Alternatively, the vent may be a pressure relief valve. Alternatively, the vent may comprise means for maintaining a pressure in the headspace that is below the pressure outside the column.

The outlet may be in the form of a pipe. The pipe may be moveable such that an upstream end of the pipe can be positioned at a selected position within the column. For example, it may be preferable that the upstream end of the pipe is positioned below the liquid level of the mobile phase in the column, but above the level of the stationary phase. Suitably, such positioning may be achieved by the use of a buoyant support near to the upstream end of the pipe, this support floating on the surface of the mobile phase and maintaining the position of the upstream end of the pipe at or below the surface of the mobile phase. Alternatively, such position may be achieved by mechanical means such as electrical or pneumatic actuators. Preferably, an electric or pneumatic linear actuator is provided outside the column in order to move the outlet pipe up or down through an optionally ring-sealed opening in the top of the column. Preferably, the column is supplied with the outlet pipe as one integrated unit. Alternatively, the column may be supplied in two parts, a sealed column and the outlet pipe, which are then assembled prior to use by insertion of the pipe through a sealed opening in the top of the column. In either case, the outlet pipe would then be connected to the pump tubing and, following the final use of the column, the column and outlet pipe would be separated from the column stand, the actuators and the pump (none of which have been in product contact) and disposed of.

Suitably, the column may be provided with the inlet, outlet and, where a vent is included, the vent sealed shut. This is particularly preferable when the column is pre-packed with a sterile stationary phase medium, as the sterility of the medium can be verified by the manufacturer and guaranteed to the user. The seals on the inlet, outlet and vent are broken before use of the column. Suitably, the inlet, outlet and vent may be re-sealable. This feature is particularly preferable where the column is intended to be disposable. Thus, the sealed column is provided containing a sterile stationary phase, the seals are broken before use, and after use the column may be re-sealed before disposing of the entire unit, preferably including the stationary phase medium. Preferably, the column may comprise a suspending phase as well as a stationary phase medium. Preferably, said suspending phase comprising a substance that is capable of inhibiting agglomeration of the stationary phase medium during shipment and/or storage of the column prior to use. This has the advantage of facilitating the formation of an expanded bed when the column is put into use. Suitable substances include glycerol, sucrose, dextran, PEG, PVP, and detergents (neutral, negatively charged, positively charged, or zwitterionic). Said suspending phase may contain a combination of two or more of the agglomeration inhibiting substances. Suitably, the concentration of the substance in the suspending phase is at least 1%, preferably 5%, preferably at least 10%, such as at least 30% or at least 50% for low molecular weight substances; at least 0.1% such as at least 0.5%, 1%, 2%, 5%, or 10% for polymers; and at least 0.01% such as at least 0.05%, 0.1%, 0.5%, 1%, 2%, or 5% for detergents.

Suitably, the inlet may be a known type of inlet adapted to provide driven stirring of the stationary phase. However, inlets not adapted to provide driven stirring may be preferable in certain circumstances, particularly where the column is intended for single use and disposal, as this minimizes the complexity and cost of production of the column, and improves its handling characteristics. A column to be provided for single use needs to be capable of being positioned and connected to the required lines as simply as possible. Further, the column should be capable of withstanding transportation without limitations on its handling.

We have now found that when using a stationary phase medium having sufficient density it is unnecessary to stir the stationary phase medium to prevent the formation of channels and turbulence in the stationary phase. Further, the provision of an inlet screen to support the stationary phase medium is unnecessary, removing the problem of blockage of such a screen. Such simplifications to the apparatus required for expanded bed adsorption chromatography allow a disposable apparatus to become feasible for the reasons given above.

Accordingly, the inventors have devised inlets that surprisingly provide a stable expanded bed without the use of driven stirring to distribute the mobile phase evenly amongst the stationary phase. Such inlets may be used in conjunction with the vented columns of the third aspect of the invention and in the method and apparatus of the first and second aspects of the invention. However, it will be appreciated by the skilled man that such inlets may also be used in non-vented columns such as those of the fourth aspect of the invention, and in methods of expanded bed chromatography using non-vented columns, such as that of the sixth aspect of the invention.

Such an inlet may be formed as an open ended pipe. The open end of the pipe may be provided such that the flow of liquid therefrom is in any desired direction, such as horizontally, vertically upward or vertically downward. Preferably, however, the inlet comprises an inlet conduit terminating in a liquid distributor having at least one opening. Preferably, the at least one opening is directed horizontally or in a downwardly-inclined direction, i.e. towards the lower end of the column at greater than 0° below the horizontal. More preferably, the at least one opening is directed at least 45° below the horizontal, such as 90° below the horizontal. Suitably, the at least one opening may be in the form of a substantially circular hole. Alternatively, the opening may be in the form of a slot. Suitably, at least one domed or conical cowl may be provided above the inlet, having its vertex directed toward the upper end of the column. Such a cowl may partially surround the inlet. Suitably, a horizontal baffle surface may be provided above or at substantially the same level as the inlet and such a surface may form the bottom of said cowl.

Alternatively, the inlet may comprise at least one tube comprising means to create a divergent flow of liquid therefrom. Suitably, such divergent flow may form a substantially conical distribution of fluid, and such conical distribution may have a half angle of at least 45°, such as 60°. Suitably, the inlet may comprise at least one nozzle. Suitably, the tube may comprise plates transverse and internal to the tube walls, which may be arranged to create a spiral flow of the liquid. Suitably, such plates may also be adapted to prevent passage of the stationary phase medium through the inlet. Suitably, such a tube may be used in conjunction with a column whose internal lower end forms a cup of decreasing radius towards the lower end of the column. Such a shape may be formed by moulding the column to the required internal shape, or by insertion of an appropriately shaped insert into the lower part of the column. In the case of an inlet comprising several tubes, it is preferred that the internal surface of the lower part of the column is formed to provide a cup of decreasing radius centred on each of the tubes.

Alternatively, the inlet may comprise at least one tube extending across the column and having at least one opening provided therein. Suitably, the at least one opening may be horizontally or downwardly facing, such as at least 0° to the horizontal, e.g. 45° to the horizontal, preferably 90° to the horizontal. Suitably, the at least one opening may be adapted to provide a divergent flow of liquid therefrom. Suitably, the inlet comprises a central hollow chamber in fluid connection with the at least one tube.

Preferably, the size of the at least one opening is large compared with that of foulants, for example particulates and insolubles, contained in the fluid to be treated. However, the at least one opening must still be small enough to provide the intended distribution of flow at a given flow rate.

Preferably the at least one opening will have a minimum size of 0.05 mm, such as at least 0.1 mm and a maximum size of 2 mm such as a maximum of 1 mm, or a maximum of 0.75 mm Preferably, there is no lateral flow of liquid through the base of the column.

Preferably, there is no aperture plate provided above the inlet.

In order for the above mentioned flow distribution devices to perform the intended distribution of flow without formation of channels it is preferred that the linear flow rate applied to the EBA column is at least 3 cm·min$^{-1}$, such as at least 4 cm·min$^{-1}$, such as at least 5 cm·min$^{-1}$ or 6, 7, 8, 9, or 10 cm·min$^{-1}$.

Suitably, the stationary phase medium has a density of at least 1.5 gml$^{-1}$, such as at least 1.8 gml$^{-1}$, for example 2.0 gml$^{-1}$. Particularly preferably, the stationary phase medium has a density of between 2.5 and 4.0 gml$^{-1}$. Preferably, the stationary phase medium has an average particle diameter of 20-200 μm, more preferably in the range of 40-160 μm, even more preferably in the range of 60-120 μm, even more preferably in the range of 70-110 μm, even more preferably in the range of 80-100 μm.

When the raw material applied to the expanded bed column is a crude fermentation broth comprising a high concentration of whole cells or cell debris it is particularly advantageous to employ a stationary phase medium having a high density combined with an average particle size resulting in acceptable expansion of the bed during operation. Thus, it is preferred that when the raw material comprise more than 5% vol/vol cells and/or cell debris such as more than 10% vol/vol, such as more than 15% vol/vol, such as more than 20% vol/vol, such as more than 25% vol/vol the density of the stationary phase medium is at least 2.8 g/ml, such as at least 3.0 g/ml, such as at least 3.5 g/ml, such as at least 4.0 g/ml, such as at least 4.5 g/ml and the average particle size is in the range of 50-110 μm such as 60-100 μm such as 70-90 μm.

Preferably, the stationary phase medium comprises steel beads or particles, or tungsten carbide beads or particles.

The flow rate, the size of the particles and the density of the particles may all have influence on the expansion of the fluid bed and it is important to control the degree of expansion in such a way to keep the particles inside the column. The degree of expansion may be determined as H/H0, where H0 is the height of the bed in packed bed mode and H is the height of the bed in expanded mode.

Preferably, the degree of expansion H/H0 in use of the stationary phase medium is in the range of 3.0 to 1.2, such as 2.5 to 1.3, 2.2 to 1.4, or 2.0 to 1.5. Preferably, the maximum value of H/H0 is 3.0, or more preferably 2.5, such as at maximum 2.2, 2.0, 1.8, or 1.6. Preferably, the degree of expansion is at least 1.2, such as at least 1.3, such as at least 1.4, such as at least 1.5.

Preferably, the maximum pressure the column is adapted to contain is 0.35 atm; such as maximum 0.30 atm; 0.25 atm; 0.20 atm; 0.15 atm; 0.10 atm; 0.05 atm.

The EBA column may preferably be made of a low cost plastic material, preferably a transparent or semi-transparent plastics material. Preferably, the plastics material also complies with the requirements for safe use in the production of pharmaceutical products with minimal leakage of toxic compounds. Examples of suitable plastics materials are polypropylene, polyethylene, TPX (methylpentene copolymer), polycarbonate, plexi-glass and PVC. The column may preferably be produced by injection moulding or extrusion.

In some situations it may be preferred to make the EBA column out of glass.

Suitably, the EBA column according to either the third or the fourth aspect of the invention may be supplied connected to two pumps, one positioned upstream of the inlet and one positioned downstream of the outlet.

The separation efficiency of chromatographic columns is often expressed in terms of the number of theoretical plates, N in a given column or normalized as the number of theoretical plates per meter of packed bed, N/m. The higher the number the better chromatographic separation efficiency the column has.

For expanded bed columns the number of theoretical plates can be determined by the Residence Time Distribution test (as described in the hand book 'Expanded Bed Adsorption', page 14-16, Edition AA, ISBN 91-630-5519-8, by Amersham Pharmacia Biotech, Sweden), which is a tracer stimulus method that can be used to assess the degree of longitudinal axial mixing (dispersion) in the expanded bed. A high theoretical plate number indicates a low degree of axial mixing (or unwanted turbulence and channelling) and thereby a high degree of separation efficiency. As also mentioned in the handbook, it is generally accepted that an efficient separation is achieved if the expanded bed column has a number of theoretical plates of N=25-30 or N/m=170-200 plates per meter of sedimented adsorbent in the column. For some applications involving simple binding and release (capture and release) it may not be necessary to have such a high separation efficiency as indicated by the N/m=170-200 number, in which cases it may be sufficient to employ a column having a theoretical plate number of 50-75 N/m.

For packed bed columns it is generally found that the theoretical plate number and thus the separation efficiency decreases when the flow rate is increased and this would also be expected for expanded bed columns when the linear flow rate approaches the terminal settling velocity of the adsorbent beads or when the mass transfer kinetics becomes the limiting factor.

Surprisingly we have found that when the column inlets according to the invention are employed in expanded bed columns containing very high density adsorbent beads the theoretical plate number remains high and even increases with an increase in the flow rate within a very broad range of flow rates that are particularly suitable for the production of proteins and other bio-molecules with high productivity.

We have now found that the specific combination of column inlets according to the invention, adsorbent density and particle size and high flow rates leads to very attractive expanded bed systems that unlike prior art solutions achieve several important tasks at the same time. Especially the combined features of the invention including the avoidance of overpressure in the column enables the production and employment of expanded bed adsorption columns having a high degree of separation efficiency (a high theoretical plate number) at high linear flow rates (i.e. high productivity per unit volume of adsorbent) in a sealable column made of a low cost material.

Thus it is particularly preferable to employ expanded bed columns according to the invention that have a theoretical plate number of at least 25, such as at least 50, 75, 100, 125, 150, or 200, when tested at a linear flow rate of at least 5 cm/min, such as at least 6 cm/min, 7, 8, 9, 10, or 15 cm/min.

Likewise, it is particularly preferable to employ expanded bed columns according to the invention that have a theoretical plate number per meter of sedimented adsorbent of at least 50 N/m, such as at least 75, 100, 125, 150, 175 or 200 N/m, when tested at a linear flow rate of at least 5 cm/min, such as at least 6 cm/min, 7, 8, 9, 10, or 15 cm/min.

Preferably, the methods according to the invention use a stationary phase medium with a density of at least 2.5 gml$^{-1}$, for example at least 3.0 gml$^{-1}$, and a flow rate of liquid through the inlet of at least 5 cm/min, such as at least 7.5 or at least 10 cm/min, when the column inlet is not adapted for driven stirring of the stationary phase medium.

Preferably, the apparatus according to the second or the fourth aspect of the invention further comprises at least a first pump upstream of the inlet and a second pump downstream of the outlet. Preferably, the pumps are peristaltic pumps.

It will be appreciated that the use of at least a first pump upstream of the inlet and a second pump downstream of the outlet may be used in conjunction with vented or non-vented columns, and in methods of conducting expanded bed absorption using vented or non-vented columns.

Preferably, the apparatus further comprises a monitor for the liquid level and/or a monitor for the level of the stationary phase medium in the column. Suitably, the or each monitor may be an ultrasound monitor or an optical monitor. Preferably, such a monitor is an ultrasound monitor.

Suitably, the apparatus further comprises a controller, suitably in the form of a linear actuator, for controlling the position of the upstream end of the outlet pipe, where that form of outlet is used, as previously described. The control of the actuator positioning the outlet pipe inside the column may preferably be coupled to the monitor measuring the liquid level and/or the level of the stationary phase medium in the column.

Suitably, the apparatus may further comprise a source of fermentation broth. Suitably, the apparatus may further comprise a receptacle for spent broth. Suitably, the apparatus may further comprise a source of eluent. Suitably, the apparatus may further comprise a means for further purification of at least one component of the fermentation broth, such as a membrane filtration apparatus.

Preferably, the regulation of the expansion of the stationary phase medium is achieved by use of a first pump upstream of the inlet for pumping said liquid into the column.

Preferably, the height of the liquid above the expanded stationary phase medium is regulated by a second pump downstream of the outlet for pumping said liquid out of the column.

Preferably, the expansion of the stationary phase medium is determined by ultrasound monitoring of the liquid level and/or the stationary phase medium level within the column. Such monitoring methods are known in the art.

Preferably, the restriction of the overpressure is achieved by means of a vent.

Preferably, the outlet comprises a pipe adapted such that an upstream end of the pipe may be moved to a selected position within the column, and the method further comprises the step of moving the upstream end of the pipe to a desired position in the column.

Preferably, the method according to the first aspect of the invention comprises the further steps of:

providing a stationary phase medium contained in a column having a lower portion comprising a sealed inlet and an upper portion comprising a sealed outlet and a sealed vent, all providing when unsealed a fluid connection between the interior and exterior of said column; and removing the seals from the said inlet, outlet and vent before supplying the liquid to the stationary phase medium. Preferably, the method according to the sixth aspect of the invention comprises the further steps of: providing a stationary phase medium contained in a column having a lower portion comprising a sealed inlet and an upper portion comprising a sealed outlet, both providing when unsealed a fluid connection between the interior and exterior of said column; and removing the seals from the said inlet and outlet before supplying the liquid to the stationary phase medium. This enables the column to be supplied pre-packed from the vendor, possibly containing not only the stationary phase medium but also a suspending phase as previously described, for example one containing an agglomeration inhibitor.

Preferably, the method according to either the first or the sixth aspect of the invention comprises the further steps of, after allowing adsorption of the at least one component:

eluting the at least one component from the stationary phase medium; and, after at least one iteration of the adsorption and elution steps, disposing of said column, preferably still containing the same stationary phase medium with which the column was first used.

Suitably, however, the method may comprise the steps of cleaning the stationary phase medium, verification of the cleanliness of the stationary phase medium, and re-use of the expanded bed apparatus after elution of the at least one component. Preferably, the cleaning and re-use takes place without including a verification step. However, verification of cleanliness may be performed by taking swabs for microbial testing at different sites inside the column and its connections, and/or by taking samples of the adsorbent and testing them for microbial contamination and/or the presence of foreign matter on the surface of the beads.

Preferably, after elution of the at least one component from the stationary phase medium, and before disposal of the column, the method comprises the step of:

re-sealing the vent (if applicable), outlet and inlet of the column.

Preferably, the at least one component of the liquid is a protein.

Preferably, the contents of the chamber are not agitated by any means other than the introduction of fluid, eluent or other liquid through the inlet.

DESCRIPTION OF THE PREFERRED EMBODIMENTS

Figure 1:
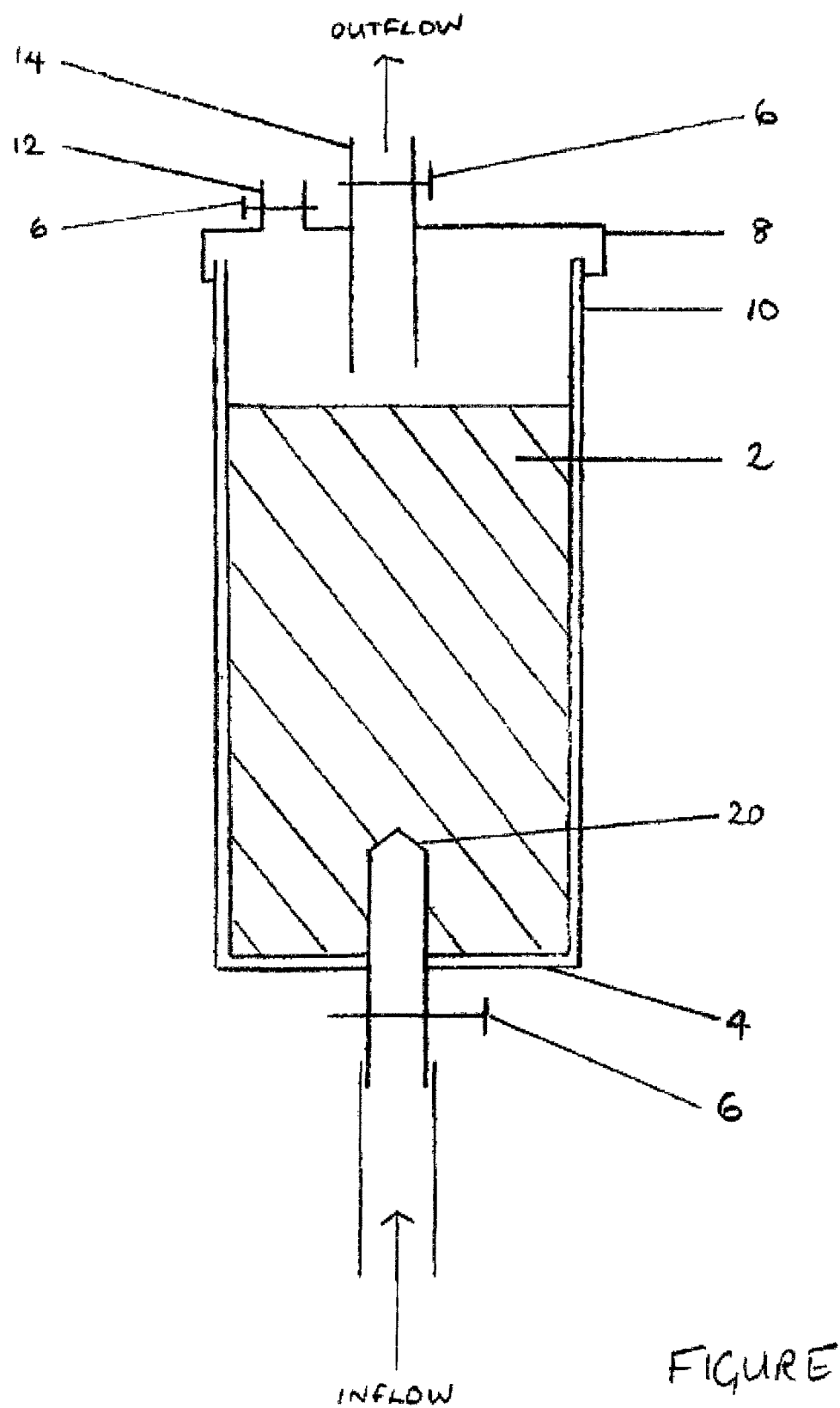
FIG. 1 shows a schematic diagram of a column for use in the invention.

Referring to FIG. 1, column 10 contains the stationary phase medium 2. It may be formed from plastics materials or glass, as described previously, in a conventional manner. For example, column 10 may be moulded from a plastics material such as polyethylene. This material is particularly preferred when column 10 is intended for a single use, as it is strong, light, disposable, and inexpensive. The column 10 is typically of a substantially cylindrical shape and limited at the lower end by a lower part 4 and at the upper end by an upper part 8. Through the lower part 4 is provided an inlet 20. Inlet 20 may be provided with a valve 6 or other suitable sealing means which prevents the escape of stationary phase 2 or the fluid that may surround it in transit, and which may be opened when the column is connected into the required apparatus for use. Similarly, through the upper part 8 is provided an outlet 14 and a vent 12, both or either of which may be provided with a valve 6 or other suitable sealing means. It is envisaged, in a preferred embodiment, that the column 10 is supplied as a single sealed unit intended for single use. Preferably, the upper closure of the column is not removable without causing damage to the column, in order to prevent attempted re-use of the column or replacement of the stationary phase medium. However, it is contemplated that the upper part 8 may be removable in order that the stationary phase may be replaced, and/or that the stationary phase may be cleaned, allowing the column 10 to be re-used.

It is envisaged that the preferred form of the vent 12 will be a simple opening in the top of the column, with the optional inclusion of a protective filter as described below. However, it is also contemplated that the vent may take the form of a pressure relief valve, such as a spring- or gravity-biased ball-valve or needle valve, in which case the pressure in the headspace will be a chosen amount above the pressure outside the column dependent on the pressure at which the valve is adapted to release the pressure in the headspace, or alternatively that the vent may take the form of a pump that maintains the headspace at a pressure below that outside the chamber.

Suitably, the stationary phase medium may be sampled by removing a small quantity via the vent or the outlet. However, where the column is intended for limited use followed by disposal, it is not envisaged that sampling of the stationary phase medium will be necessary.

FIG. 2A shows a section of column 10 taken along the line X-X in FIG. 2C, which shows column 10 from above. FIG. 2B shows the section 2A in a perspective view. FIGS. 3-12A-C are arranged in a similar manner.

Figure 2:
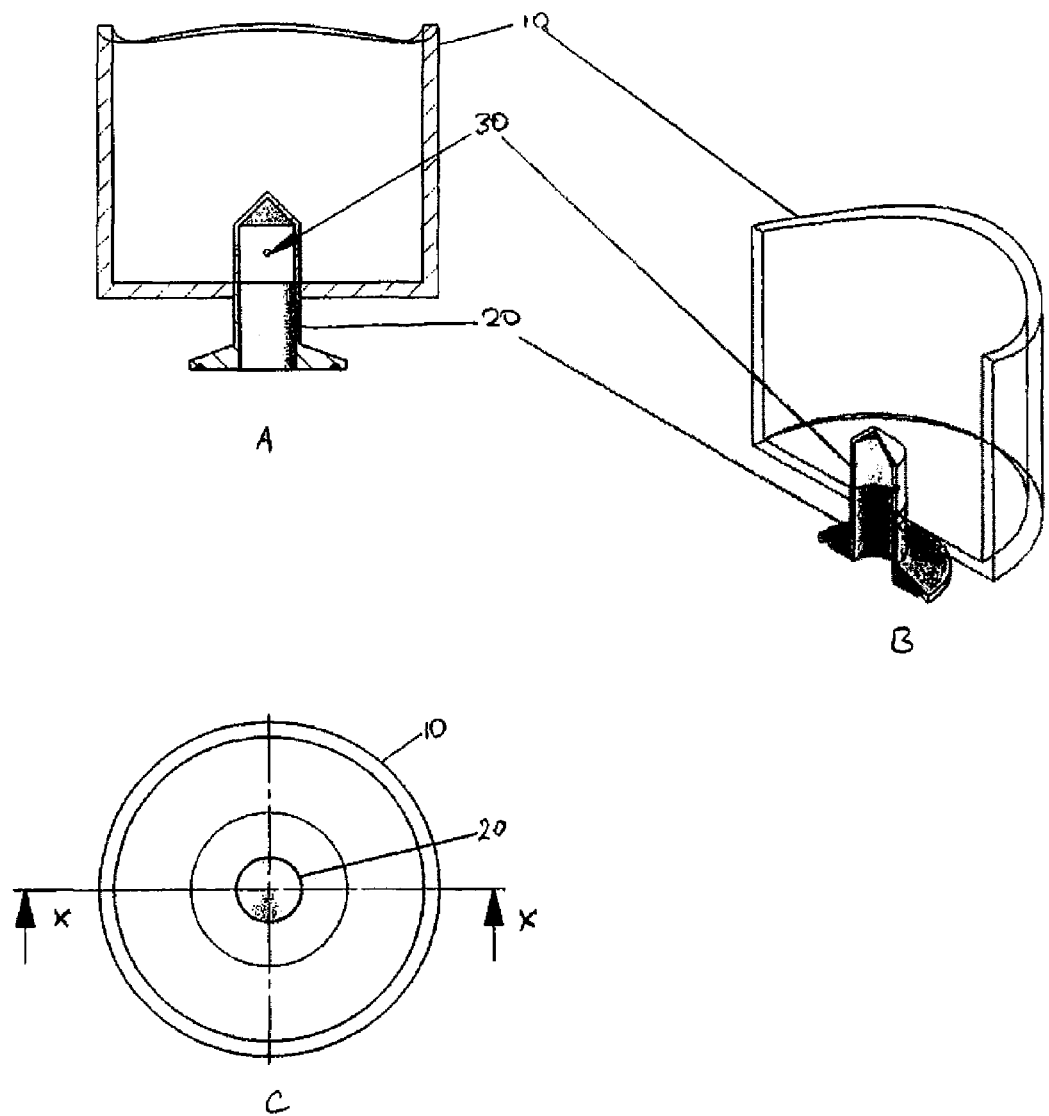
FIGS. 2 to 12 show alternative fluid delivery means of the invention.

FIG. 2 shows the lower section of column 10 shown in FIG. 1. Inlet 20 is shown here as a closed tube having small openings 30 in its vertical surface. The closed end of inlet 20 is depicted as having a conical shape; it will be appreciated by the skilled man that other shapes of the closed end may be substituted. The openings 30 are preferably large relative to the size of any particulates or other insoluble matter present in the liquid to be treated. This provides the advantage of not requiring a preliminary filtration or clarification step before introducing the liquid to the column 10, thus simplifying and shortening the purification process. The openings 30 are also preferably angled downwards in order that they are not blocked by the stationary phase particles (not shown) surrounding inlet 20, and also to direct the turbulence produced by the jets of liquid in the stationary phase by limiting the jets to the very bottom of column 10. This further permits the openings 30 to be significantly larger than the expected size of any particulates in the fluid without the problem of the stationary phase medium blocking the openings or passing through the openings 30 into the inlet 20. Thus, the likelihood of blockages of the openings 30 caused by either the particulates in the liquid or the stationary phase medium is minimised.

Figure 3:
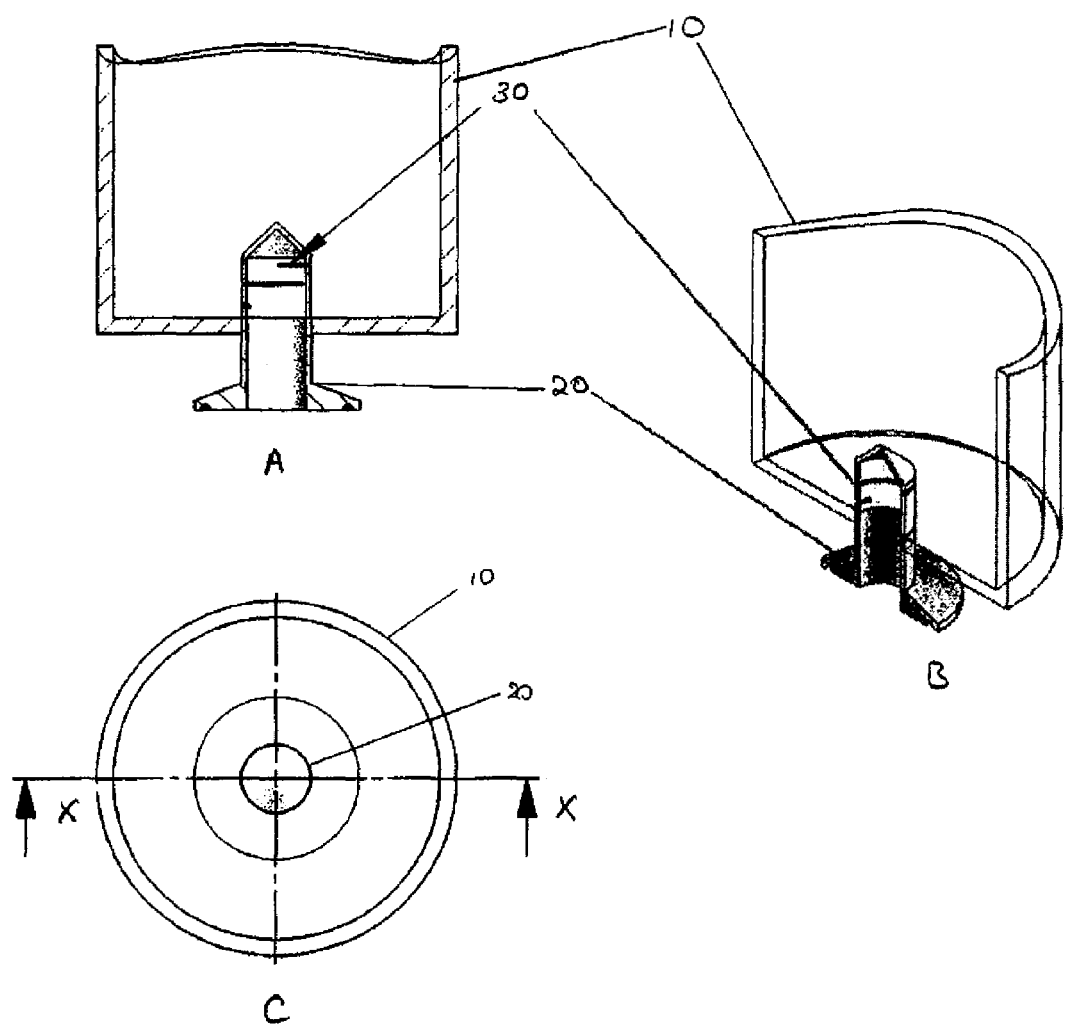

FIG. 3 shows an alternative embodiment of the inlet 20 in which the openings 30 are in the form of slots. Again, the size of the openings is preferably large relative to any insoluble matter in the fluid, and the openings are preferably directed downwards.

Figure 4:
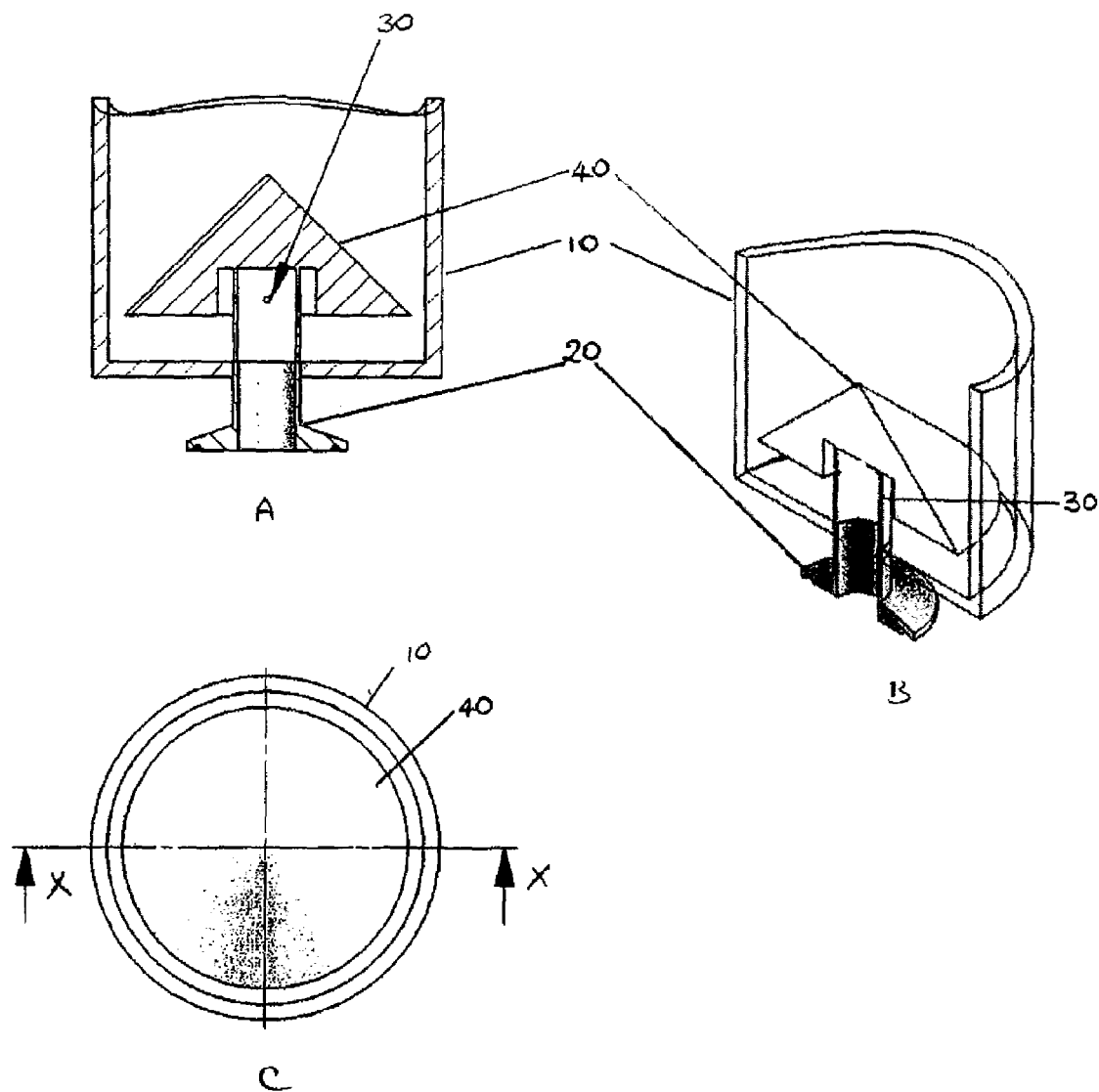
Figure 5:
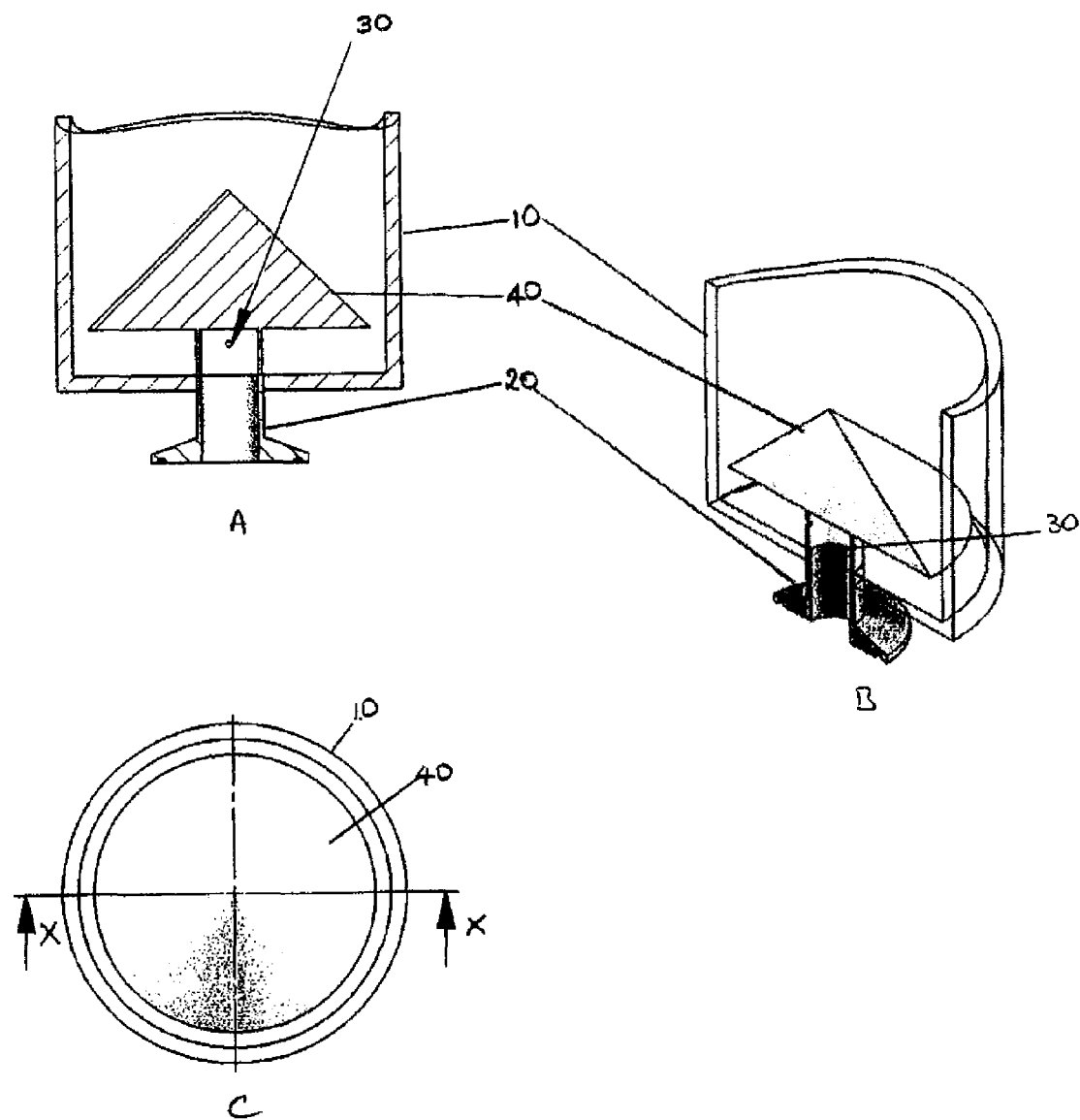

FIGS. 4 and 5 show the inlet of FIG. 2, but with the addition of conical cowl 40. Conical cowl 40 functions to direct the liquid downwards to the bottom of the column 10 after exiting the openings 30, and allows the liquid to flow uniformly around the base of the cone and up the stationary phase to the top of the column. Further, turbulence and channelling of the stationary phase 2 is minimised as those parts of the stationary phase near to the openings 30 are separated from the bulk of the stationary phase by the horizontal (lower) baffle surface of conical cowl 40. It can be seen from the Figures that the cowl 40 may function as the end cap of the tube forming inlet 20, and that the cowl may surround the openings 30 (as in FIG. 4) or be positioned above the openings (as in FIG. 5).

Figure 6:
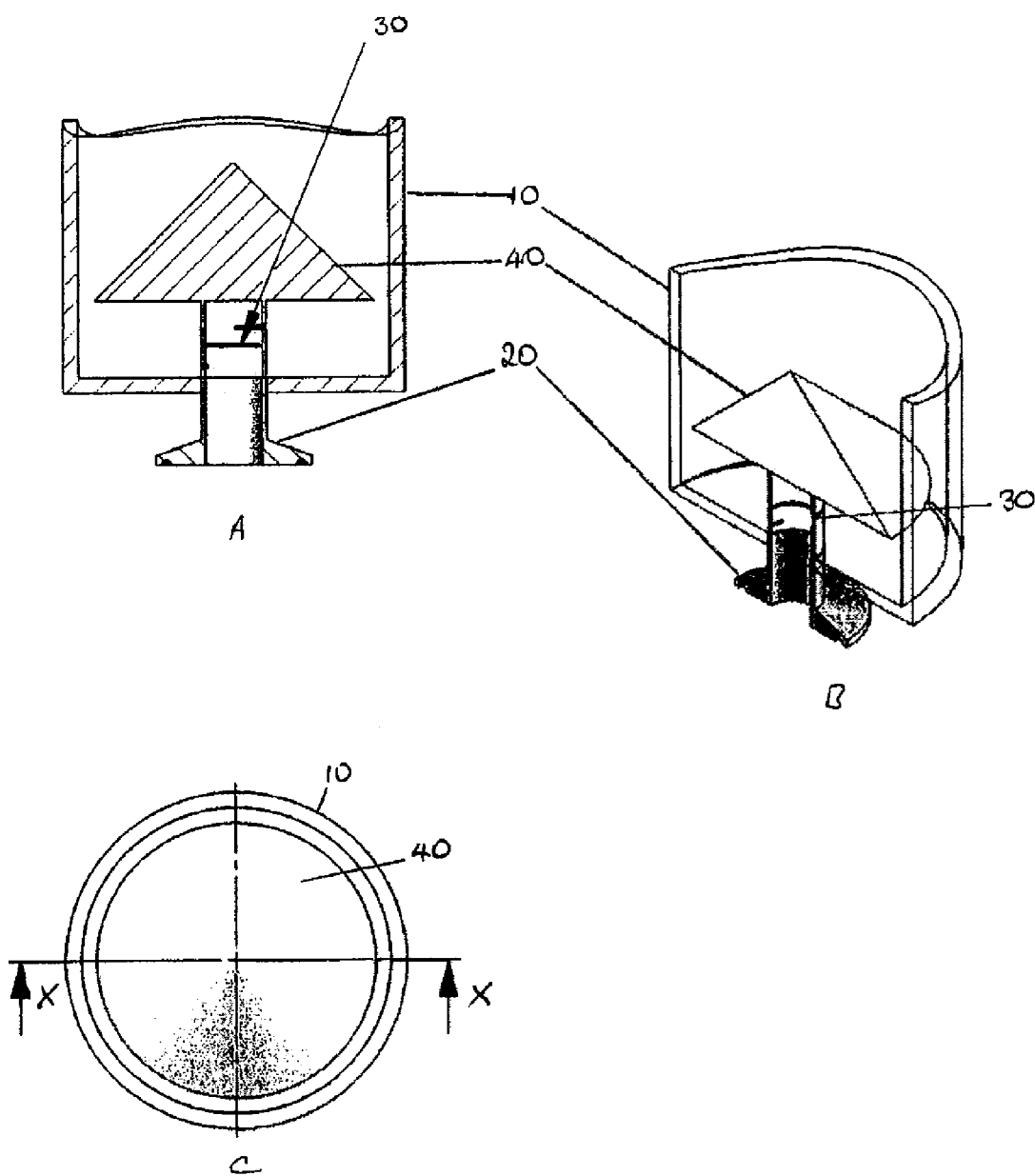

FIG. 6 shows a conical cowl 40 as in FIG. 5 in combination with the inlet shown in FIG. 3.

Figure 7:
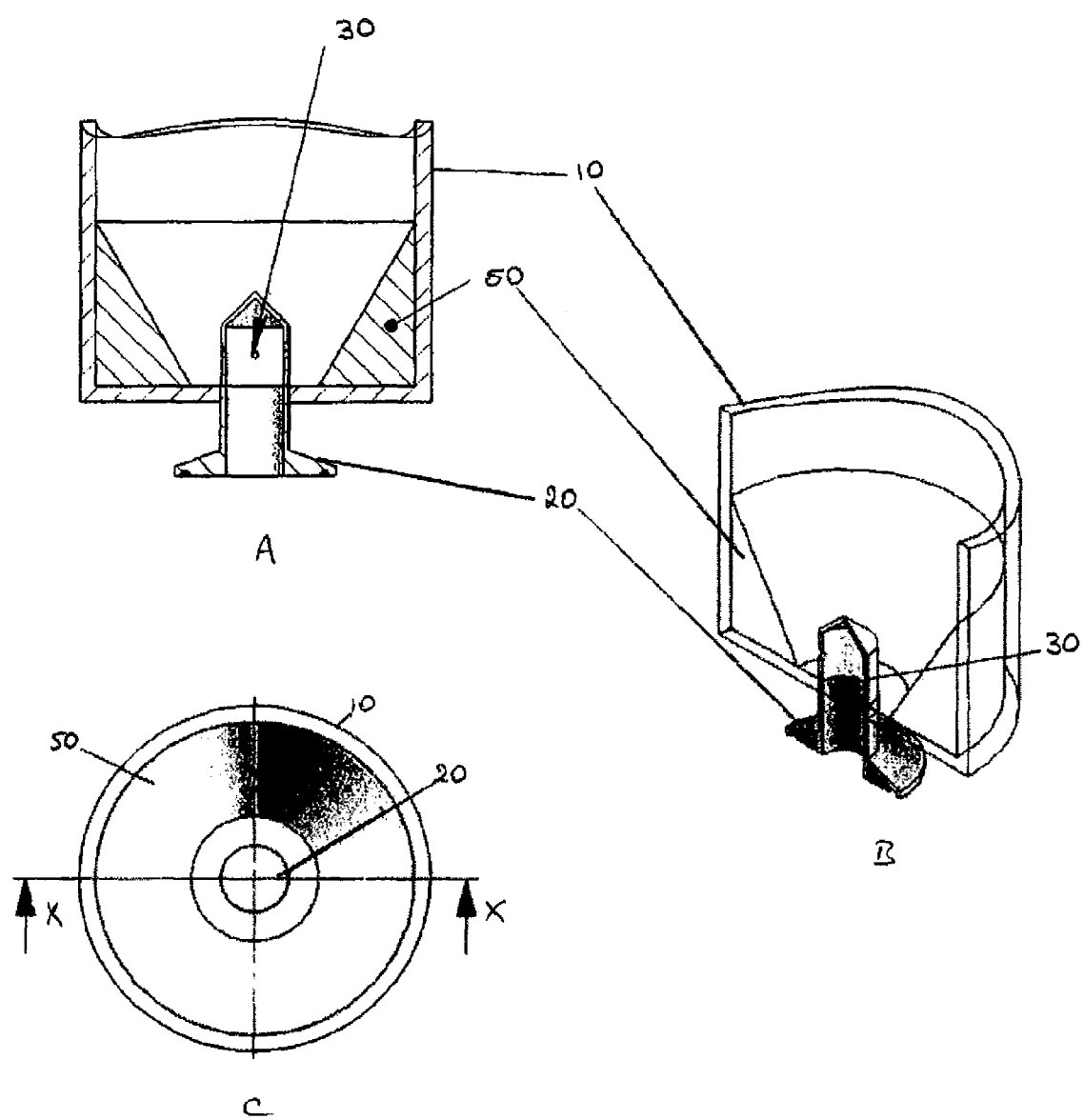

FIG. 7 shows the inlet of FIG. 2 in combination with a conical insert 50 which reduces the volume of the column 10 at its lower end, and thus the volume of stationary phase surrounding the inlet 20. The turbulence of the stationary phase created in the conical volume decreases the likelihood of developing "dead space" in the column due to the presence of stationary phase not brought into contact with the liquid and therefore not forming part of the expanded bed. It is envisaged that the internal shape of the lower part of the column 10 achieved by use of the insert 50 may be alternatively achieved by moulding of the lower part of the column to have the required tapering shape on the inner face.

Figure 8:
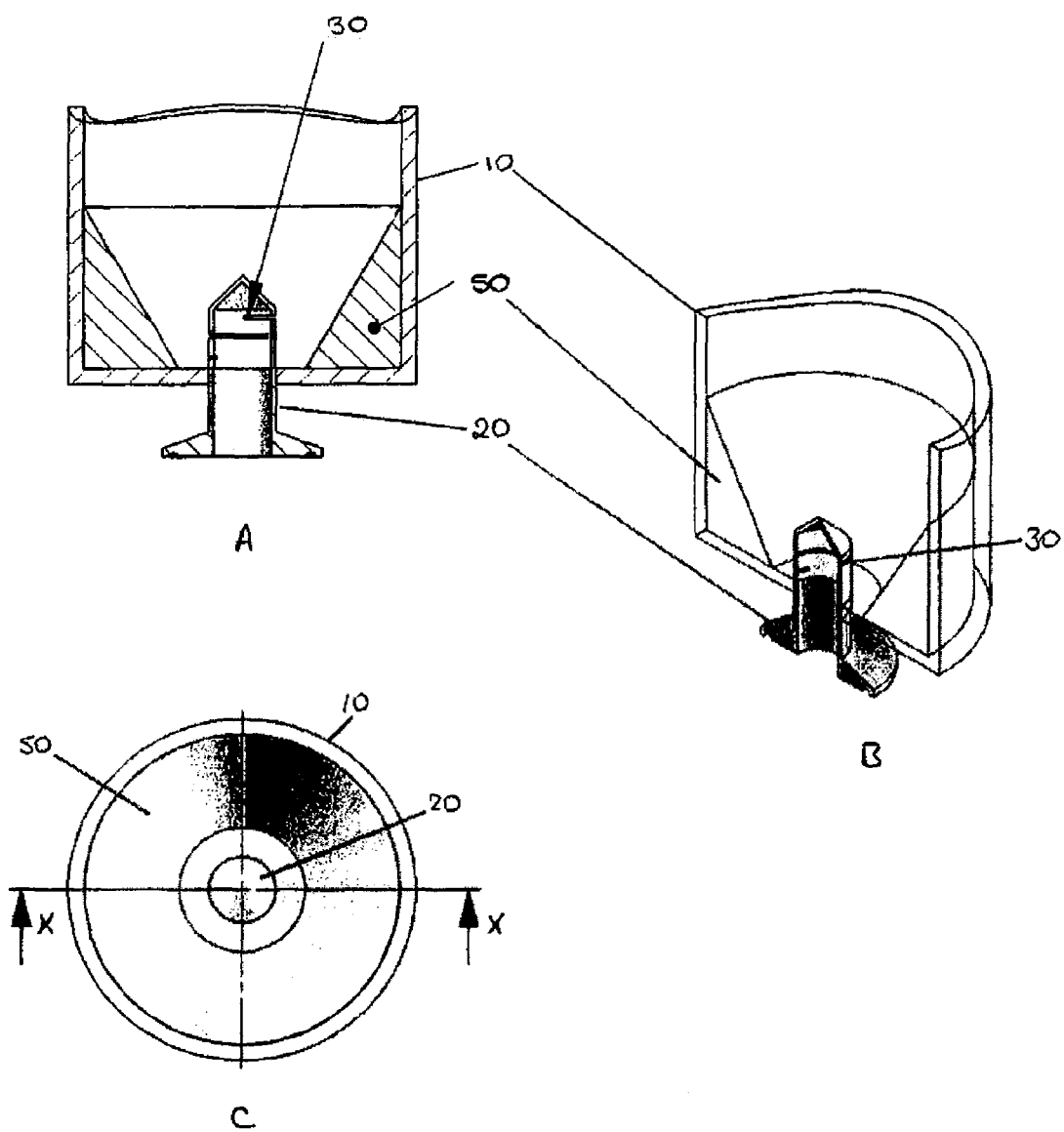

FIG. 8 shows the inlet of FIG. 3 in combination with conical insert 50.

Figure 9:
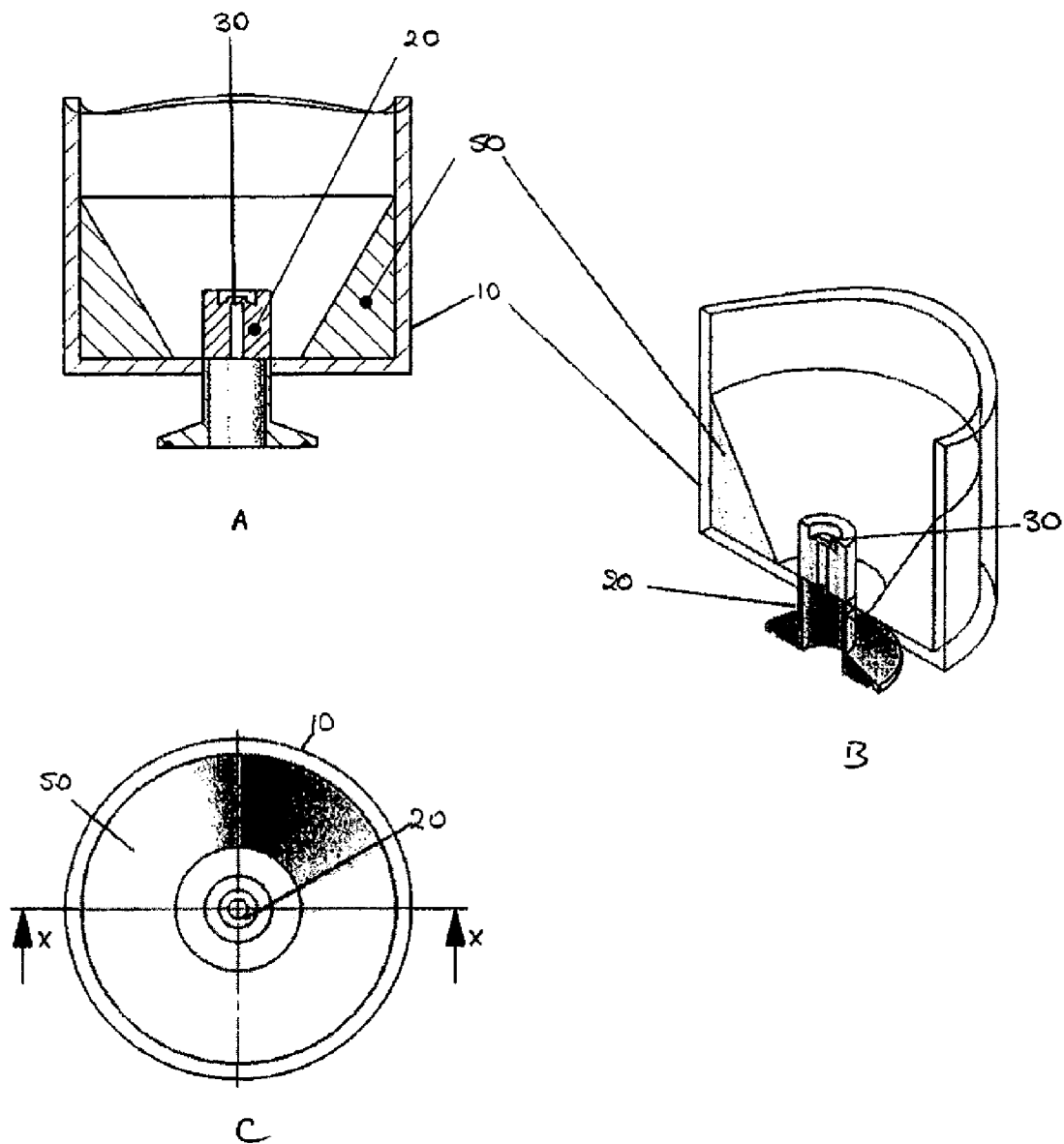

FIG. 9 shows an alternative embodiment of inlet 20, in which the opening 30 is in the form of a nozzle adapted to provide a diffuse, divergent jet of liquid. Suitably, the half angle of the cone described by the jet of liquid may be at least 45°, for example 60°. Preferably, such a nozzle is used in conjunction with the conical insert 50 shown in the Figure, in order that the dead space in the column is minimised. The half angle described by the sloping faces of conical insert 50 may suitably be substantially the same as that described by the jet of liquid in order that the maximum possible amount of the stationary phase 2 is brought into contact with the liquid.

Figure 10:
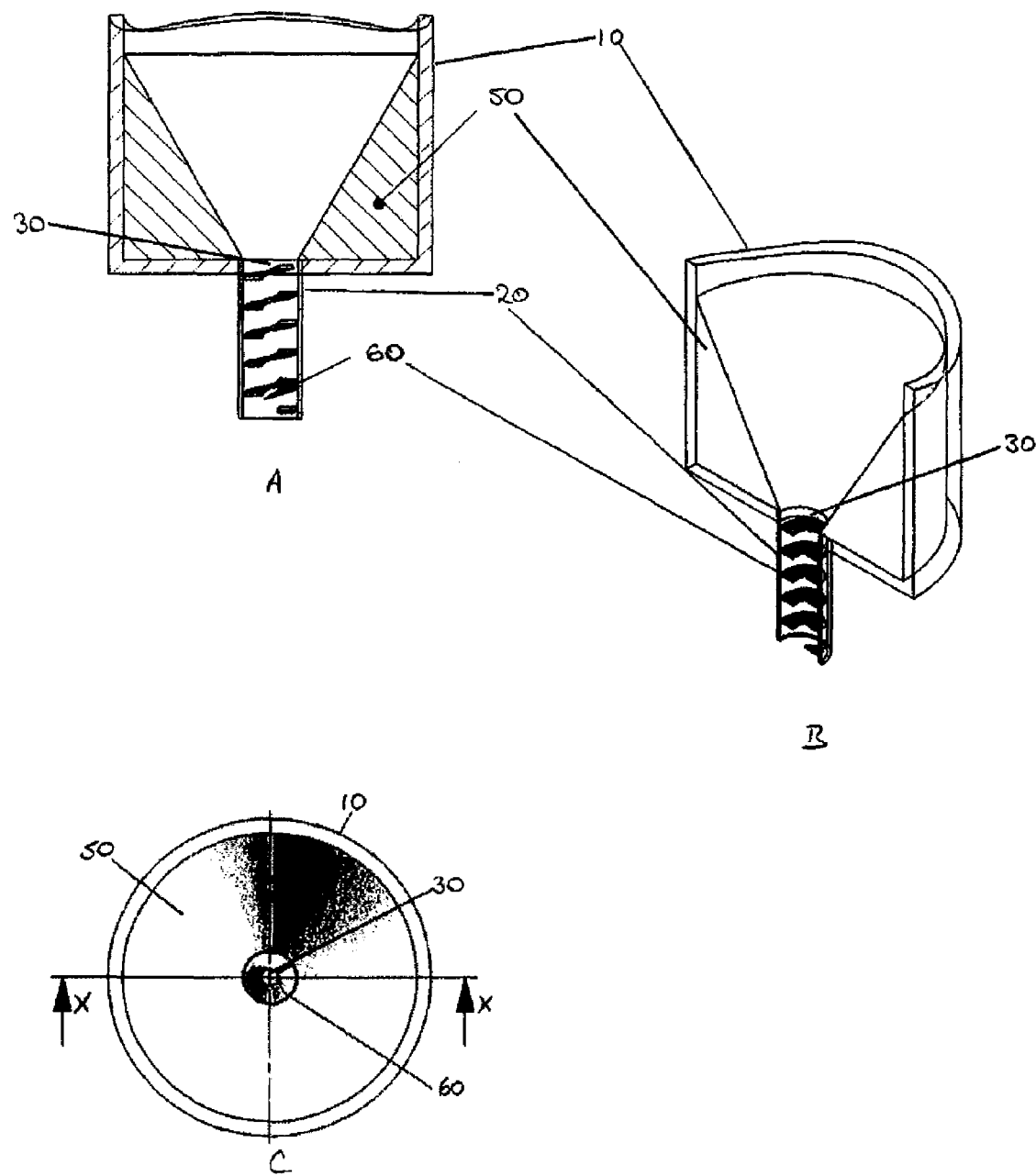

FIG. 10 shows an alternative embodiment of inlet 20, in which the inlet is a tube provided with plates 60 on the interior wall adapted to cause the liquid passing through the tube to spin. The opening 30 is level with the lower part 4 of column 10, and is not constrained but is of the same diameter as the tube 20. Thus, the spinning liquid, on reaching opening 30, will form a divergent jet, and will be distributed widely within the column 10. Preferably, this inlet is used in conjunction with a conical insert 50 having its smaller opening of the same diameter as that of opening 30. The divergent jet can thereby contact substantially all of the stationary phase in the vicinity of the opening 30, avoiding the formation of dead space in the column. In the absence of the conical insert 50, it is unlikely that the divergent jet produced by opening 30 would be sufficiently divergent to contact the stationary phase occupying the cross-hatched area in FIG. 10A. The jet of liquid produced by the inlet 20 should be sufficiently diffuse that no significant channelling is caused in the stationary phase by the jet.

Figure 11:
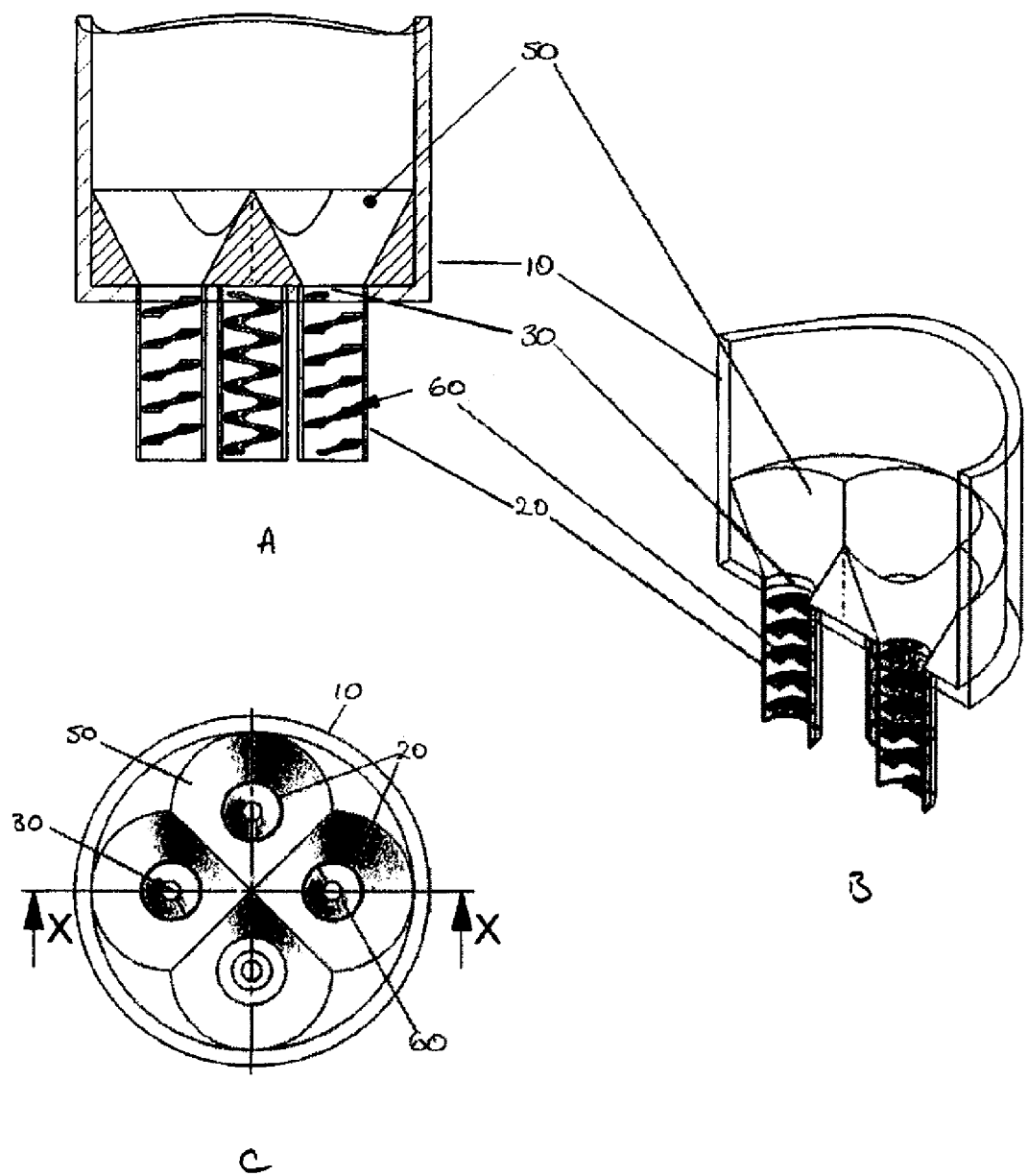

FIG. 11 shows a column 10 having four of the inlets 20 shown in FIG. 10. This arrangement is suitable for a column of large diameter, such as at least 20 cm in diameter. Additionally, the division of the stream of liquid into four allows the liquid to be distributed more evenly throughout the lower part of the column 10. Such an arrangement of a plurality of inlets may use any of the above described embodiments of the inlets.

Figure 12:
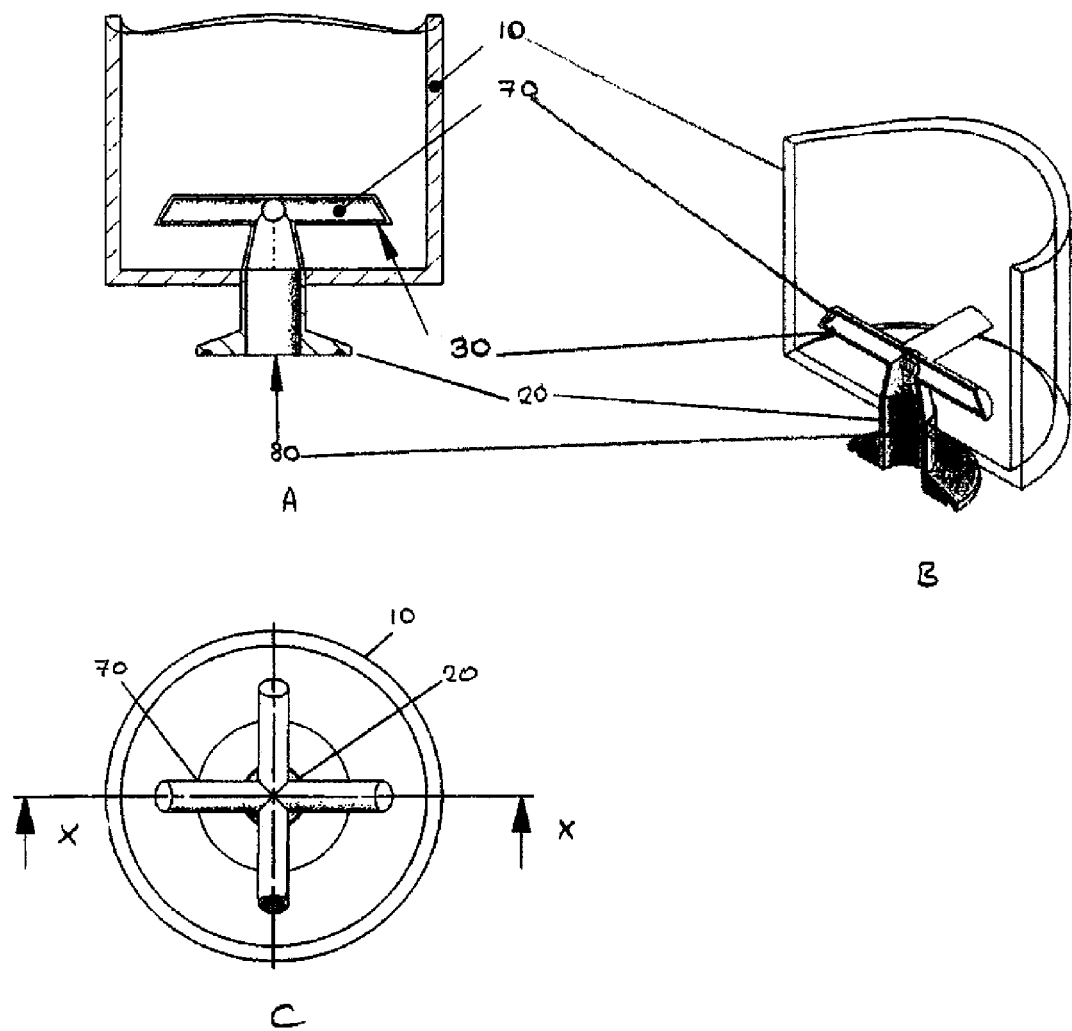

FIG. 12 shows an alternative inlet 20, which comprises tubes 70 extending radially within column 10. Openings 30 are provided in the tubes 70. The liquid to be treated is supplied via a central tube 80 to the radial tubes 70 and passes through and out of the openings 30. Preferably, the openings are directed downwards, for reasons outlined above. A plurality of openings may be provided on each of the tubes 70, and a plurality of tubes 70 may be provided. Again, the openings are preferably large relative to any particulate or insoluble matter in the liquid to be treated.

The stationary phase 2 must have a density of at least 1.5 $gml^{-1}$ in order that the distributors of the invention do not cause instability and turbulence in the stationary phase expanded bed, which would result in lower performance of the stationary phase. The average particle size of the stationary phase medium may be in the range 20 to 200 μm. Suitable stationary phases include those described in WO 92/00799 and WO 00/57982.

Figure 13:
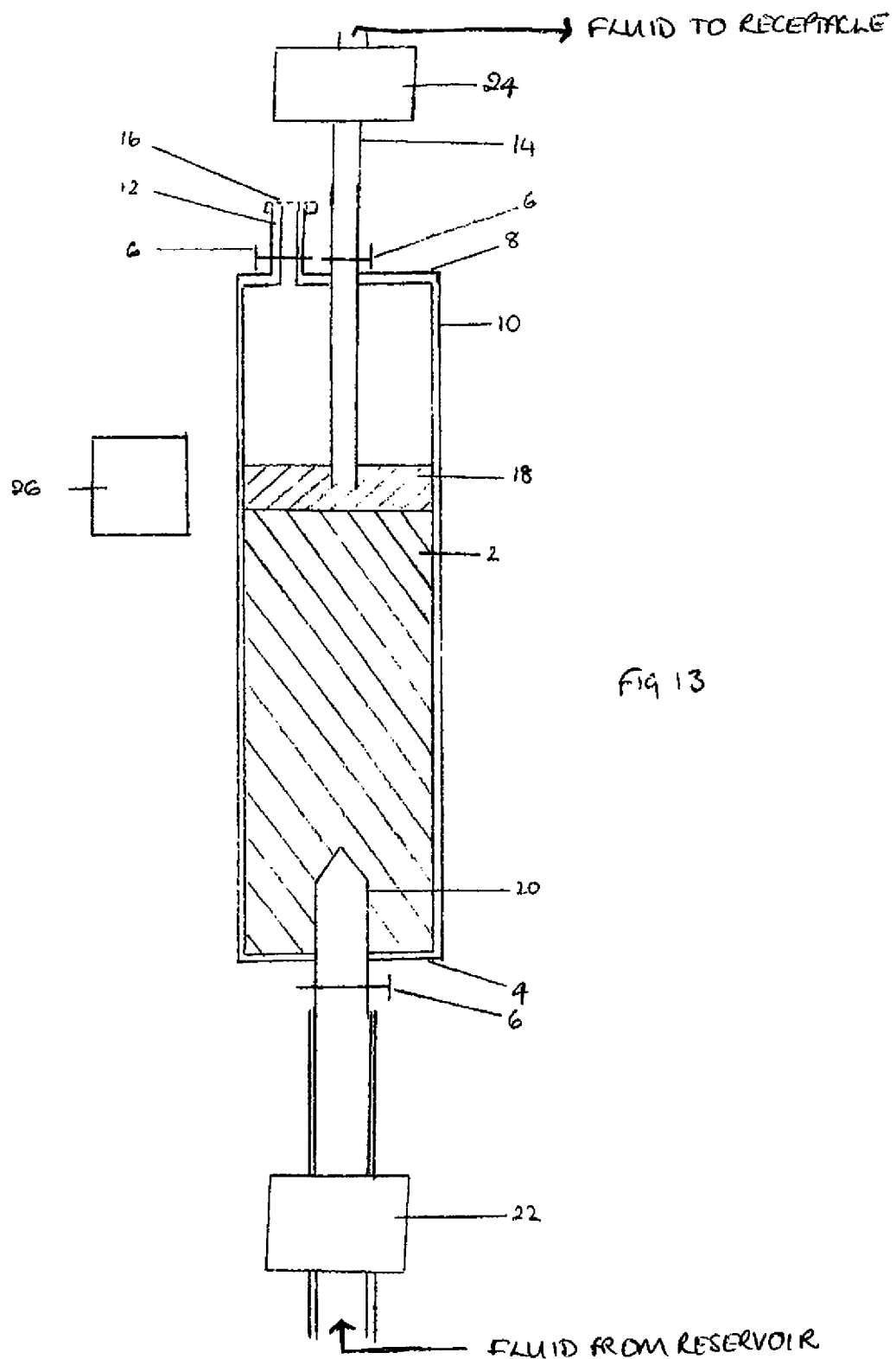
FIG. 13 shows a schematic diagram of an apparatus of the invention.

FIG. 13 shows a schematic representation of an apparatus for conducting expanded bed chromatography according to the second aspect of the invention. The apparatus includes a column 10, having an inlet 20, outlet 14 and vent 12, and containing stationary phase medium 2.

In this Figure, vent 12 is depicted with a filter 16 provided over the opening therein. Such a filter may be used to prevent the entrance and/or exit of contaminants, such as dust and microbes, to and/or from the column 10. A suitable filter may be a microfilter such as a general gas filter from Pall Corp. [product number 9004500 Pallflex media, 4.8 to 3.2 mm (3/16 to 1/8 in) HB] or an Intervene™, Intervene High-Flow filter from Pall Corp.

The inlet 20 may be an inlet not adapted for driven stirring of the column contents, such as those described above in relation to FIGS. 2 to 12, or may be another known type of inlet, such as a mechanically-driven rotating inlet or a magnetically driven rotating inlet. Inlets of this type are described in WO99/65586.

The inlet 20, outlet 14 and vent 12 are each shown with a valve 6 that may close and seal the inlet, outlet and vent before use of the column and after use of the column. In this way, the column contents may be kept sterile before use of the column, and, where the column is intended to be supplied pre-packed with stationary phase for a single use or a limited number of uses followed by disposal, the column may be supplied in a verified sterile state by the supplier and may be closed after use to facilitate safe disposal of the contents.

The outlet 14 is here shown in the form of a pipe that may be moved to a desired level within the column. This pipe may be provided integrally with the outlet 14, or may be a separate item led through an outlet 14 as shown in FIG. 1. The interface between pipe and the outlet 14 may be sealed with a lip-seal allowing the pipe to glide up and down without any macroscopic contaminants entering or leaving the column. The outer part of the pipe (the part of the pipe that is positioned outside the column but may enter the inside when the position of the pipe is adjusted downwards) may further be covered by fixed flexible tubing, optionally flushed with a sterile gas, in order to prevent even microbial or chemical contaminations. It is desirable that the upstream end of the outlet is placed below the level of the liquid 18 and above the upper level of the stationary phase 2 during use of the column. Means (not shown) are therefore provided to allow the movement of the upstream end of outlet 14 to a suitable position within the column. This may be achieved by a motor-driven, user-operated means; by use of a buoyant support that maintains the upstream end of outlet 14 at or slightly below the liquid 18 level; or, preferably, a motor-driven means responsive to feedback from monitor 26 that monitors the level of the liquid 18 and/or the level of the stationary phase 2. Such a motor-driven means could be a linear actuator, which may be a pneumatic actuator or an electric actuator.

The monitor 26 may be any form of monitor capable of monitoring the liquid and/or stationary phase level within the column. For example, the monitor may be an optical monitor. However, as the liquid 18, the stationary phase 2, and/or the material from which the column 10 is constructed may be opaque either individually or in combination, it is preferred to use an ultrasound monitor as monitor 26. The monitor may provide feedback to any or all of: the pump 22 upstream of inlet 20; the pump 24 downstream of outlet 14; and the controller (not shown) for positioning the upstream end of outlet 14.

Upstream of inlet 20 and downstream of outlet 14 are provided pumps for delivering liquid to the column via the inlet and driving liquid from the column via the outlet. These pumps may be any suitable pumps known in the art. However, it is preferred to use peristaltic pumps in order that the liquid does not contact any part of the pump itself. Examples of suitable peristaltic pumps include Watson-Marlow Bredel Sanitary Pumps or Masterflex peristaltic pumps from Cole-Parmer. The use of peristaltic pumps contributes to the aim of providing single use apparatus for the purification of liquids, as tubing passing through the pumps and connecting to the inlet and outlet of the column may be used once and disposed of, without the necessity of cleaning the pump.

In use, the column 10 is placed amongst the apparatus and connected at the inlet to tubing leading to pump 22, and at the outlet to tubing leading to pump 24. The seals on the inlet 20, outlet 14 and vent 12 are then broken. The liquid to be treated is driven through the inlet 20 by pump 22 to be evenly distributed amongst the stationary phase 2 at the lower end of the column 10. The liquid then flows upward through the stationary phase 2, causing expansion of the stationary phase, and is driven out of the outlet by pump 24. The flow rate of the liquid should be balanced with the density and particle size of the stationary phase in order that the stationary phase 2 is expanded sufficiently to form a stable expanded bed but does not overflow the top of the column 10. The required flow rate is maintained by the use of two pumps, one pump 22 upstream of the inlet 20 of the column 10 and a second pump 24 downstream of the outlet 14 of the column 10. The expansion of the stationary phase and the liquid level above the level of the stationary phase are monitored using monitor 26. Monitor 26 may provide feedback to the two pumps 22 and 24 in order that the flow rates of these pumps may be individually controlled to achieve the desired degree of expansion of the stationary phase and level of liquid above the stationary phase. In addition, the use of accurate flow meters, such as mass flow meters, to determine the flow rate into the inlet and out of the outlet facilitates independent manual control of the system. The degree of expansion is governed by the flow rate into the column and so is essentially controlled by the inlet pump. The height of the liquid above the expanded medium can be controlled by temporarily decreasing the flow rate through the outlet pump to increase the liquid level, and temporarily increasing the flow rate through the outlet pump to decrease the liquid level. In addition, monitor 26 may provide feedback to a controller (not shown) that determines the position of the upstream end of outlet 14, in order that the upstream end of the outlet is maintained in a desired position, such as below the liquid level but above the level of the stationary phase, during expansion and use of the stationary phase. Alternatively, however, the position of the upstream end of outlet 14 may be determined by the operator of the column, or may be determined by use of a buoyant support that maintains the upstream end of the outlet 14 in a selected position relative to the liquid surface, such as a small distance below the liquid surface.

During the expansion of the stationary phase, and any subsequent adjustment of the level of the liquid and/or stationary phase within the column 10, the pressure of the air above the liquid level in the column is allowed to equilibrate with the pressure outside the column by means of the vent 12. Thus, the column may be operated without any significant pressure build-up. This permits the use of lighter materials for the construction of the column 10 than have usually been used in the art, as there is no need for the upper part of column 10 to withstand pressures significantly above ambient pressure.

Preferably, the column 10 and stationary phase 2 are used in expanded bed form both for the adsorption of the compound(s) of interest and for its elution.

Example 1

Determination of Theoretical Plate Number in Expanded Bed Columns According to the Invention An expanded bed adsorption column was generally assembled as illustrated in FIG. 13 but having an inlet according to FIG. 9 (height of cone being 15 cm) and connected to two peristaltic tube pumps (Watson Marlow). It contained a volume of adsorbent equal to a sedimented bed height of 25 cm. The adsorbent consisted of agarose-tungsten carbide conglomerate beads having an average particle size (d (0.5)) by volume of 149 µm and a density of 3.1 g/ml. The adsorbent was suspended in a 25% glycerol solution in order to avoid clumping and dense packing. Just prior to use the column was washed with 30 bed volumes of deionised water.

The column was tested by the determination of the number of theoretical plates per meter (residence time distribution measurement, RTD) as a function of flow rate.

The negative step input method as described in the handbook 'Expanded Bed Adsorption', page 14-16, Edition AA, ISBN 91-630-5519-8, by Amersham Pharmacia Biotech, Sweden, and which is commonly used by those skilled in the art of expanded bed adsorption was used for assessing the performance of the system.

A solution of acetone (0.5% in water) was pumped into the column at a predetermined flow rate and the breakthrough of acetone at the outlet of the column was followed by continuous measurement and recording of the absorbency of the fluid at a wavelength of 280 nm (UV light). When the acetone was coming out of the column with a constant concentration according to the UV signal, the fluidising solution was switched from acetone back to water. The washing with water was performed with the same flow rate as during loading the acetone solution. Washing the column with water was continued until all acetone was washed out according to the recorded UV signal, the experiment was stopped and the number of plates per meter was calculated/determined from the recorded UV signal and plotted as a function of the flow rate applied.

Figure 14:
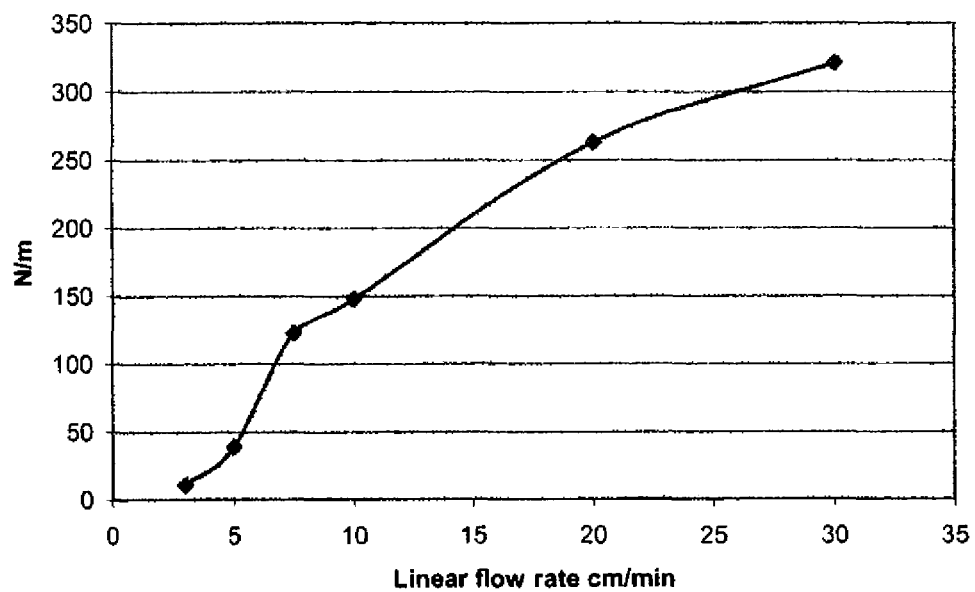
FIG. 14 shows the experimental results of Example 1.

The experiment was repeated using a range of different flow rates according to the table below and the relation between flow rate and observed theoretical plate number was recorded as illustrated in the table below and in FIG. 14.

| Linear Flow rate cm/min | Theoretical plate number N/m |
|---|---|
| 3.0 | 11 |
| 5.0 | 39 |
| 7.5 | 123 |
| 10 | 148 |
| 20 | 263 |
| 30 | 321 |

The result of the experiment indicate that the static distributor and the fluid bed system had an increasing theoretical plate number (N) per meter settled bed of solid phase support throughout the flow rate regimen investigated. It is further demonstrated that a flow rate above 5 cm/min is necessary in order to obtain a theoretical plate number of at least 100 N/m.

Example 2

Determination of Theoretical Plate Number in Expanded Bed Columns According to the Invention An expanded bed adsorption column was assembled as in Example 1, but with an inlet according to FIG. 8 (height of cone being 15 cm). It contained a volume of adsorbent equal to a sedimented bed height of 25 cm. The adsorbent consisted of agarose-tungsten carbide conglomerate beads having an average particle size (d (0.5)) by volume of 130 µm and a density of 2.8 g/ml. The adsorbent was suspended in a 25% glycerol solution in order to avoid clumping and dense packing. Just prior to use the column was washed with 30 bed volumes of deionised water.

The column was tested by the determination of the number of theoretical plates per meter (residence time distribution measurement, RTD) as a function of flow rate as described in example 1.

Figure 15:
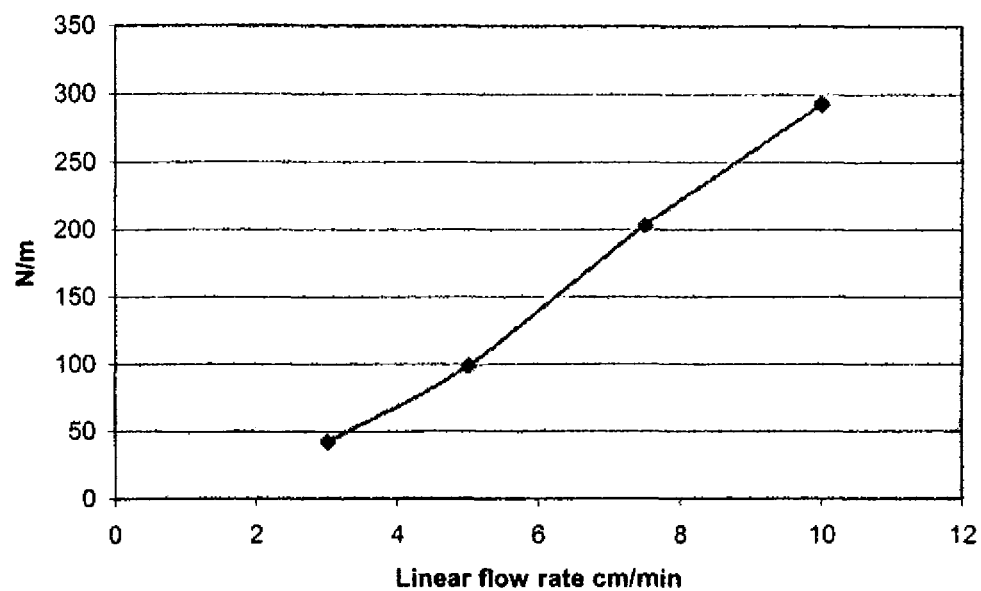
FIG. 15 shows the experimental results of Example 2.
Figure 16:
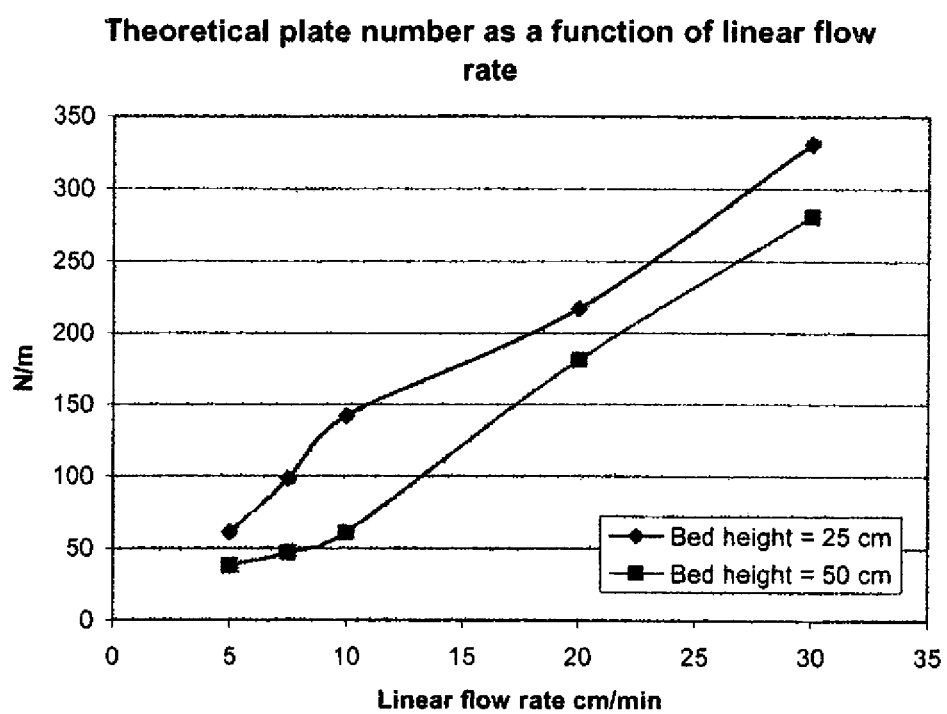
FIG. 16 shows the experimental results of Example 3.
Figure 17:
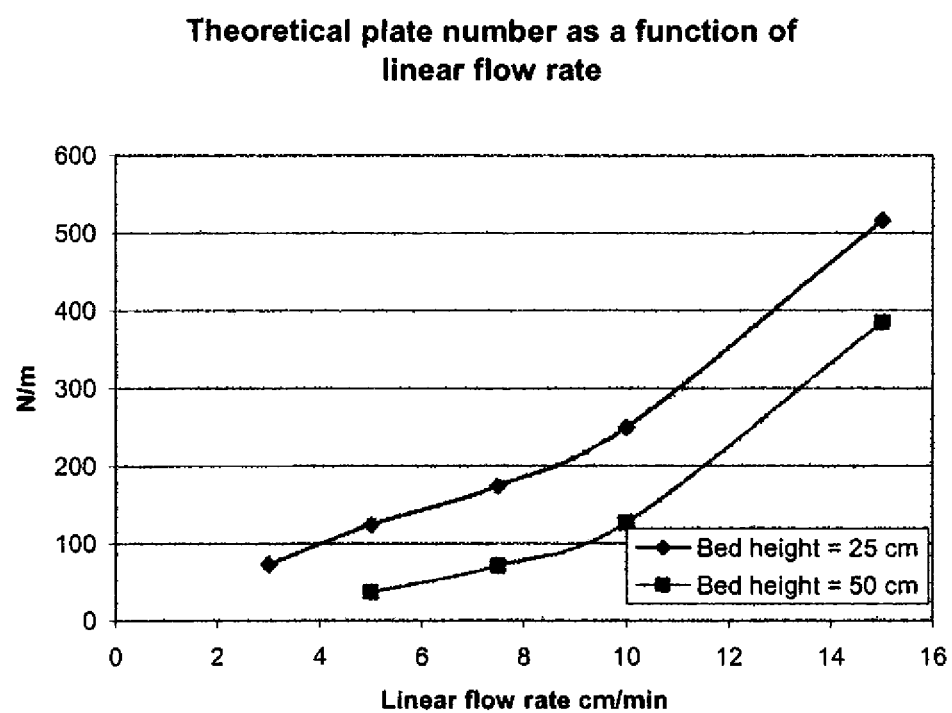
FIG. 17 shows the experimental results of Example 4.

The experiment was repeated using a range of different flow rates according to the table below and the relation between flow rate and observed theoretical plate number was recorded as illustrated in the table below and FIG. 15.

| Linear Flow rate cm/min | Theoretical plate number N/m |
|---|---|
| 3.0 | 42 |
| 5.0 | 99 |
| 7.5 | 203 |
| 10 | 293 |

The result of the experiment indicate that the static distributor and the fluid bed system had an increasing theoretical plate number (N) per meter settled bed of solid phase support throughout the flow rate regimen investigated. It is further demonstrated that a flow rate above 5 cm/min is necessary in order to obtain a theoretical plate number of at least 100 N/m.

Example 3

Determination of Theoretical Plate Number in Expanded Bed Columns According to the Invention An expanded bed adsorption column was assembled as in Example 1, except that it was fitted with an inlet according to FIG. 3 (no cone). It contained a volume of adsorbent equal to a sedimented bed height of 25 cm. The adsorbent consisted of agarose-tungsten carbide conglomerate beads having an average particle size (d (0.5)) by volume of 149 µm and a density of 3.1 g/ml. The adsorbent was suspended in a 25% glycerol solution in order to avoid clumping and dense packing. Just prior to use the column was washed with 30 bed volumes of deionised water.

The column was tested by the determination of the number of theoretical plates per meter (residence time distribution measurement, RTD) as a function of flow rate as described in example 1.

The experiment was repeated using a range of different flow rates according to the table below and the relation between flow rate and observed theoretical plate number was recorded as illustrated in the table and figure below. The experiment was further repeated using a volume of adsorbent equal to a sedimented bed height of 50 cm.

| Linear Flow rate cm/min | Theoretical plate number N/m (25 cm bed height) | Theoretical plate number N/m (50 cm bed height) |
|---|---|---|
| 5.0 | 61 | 38 |
| 7.5 | 98 | 47 |
| 10 | 142 | 61 |
| 20 | 217 | 181 |
| 30 | 331 | 281 |

The result of the experiment indicates that the static distributor and the fluid bed system had an increasing theoretical plate number (N) per meter of settled bed of solid phase support throughout the flow rate regimen investigated. It is further demonstrated that a flow rate above 7 cm/min is necessary in order to obtain a theoretical plate number of at least 100 N/m when the settled bed height of the adsorbent is 25 cm, while a flow rate above 13 cm/min is necessary in order to obtain a theoretical plate number of at least 100 N/m when the settled bed height of the adsorbent is 50 cm.

Example 4

Determination of Theoretical Plate Number in Expanded Bed Columns According to the Invention An expanded bed adsorption column (10 cm diameter) was assembled as described in Example 3. The adsorbent consisted of agarose-tungsten carbide conglomerate beads having an average particle size (d (0.5)) by volume of 130 µm and a density of 2.8 g/ml. The adsorbent was suspended in a 25% glycerol solution in order to avoid clumping and dense packing. Just prior to use the column was washed with 30 bed volumes of deionised water.

The column was tested by the determination of the number of theoretical plates per meter (residence time distribution measurement, RTD) as a function of flow rate as described in example 1.

The experiment was repeated using a range of different flow rates according to the table below and the relation between flow rate and observed theoretical plate number was recorded as illustrated in the table and figure below. The experiment was further repeated using a volume of adsorbent equal to a sedimented bed height of 50 cm.

| Linear Flow rate cm/min | Theoretical plate number N/m (25 cm bed height) | Theoretical plate number N/m (50 cm bed height) |
|---|---|---|
| 3.0 | 73 | ND |
| 5.0 | 124 | 37 |
| 7.5 | 174 | 71 |
| 10 | 249 | 127 |
| 15 | 516 | 384 |

The result of the experiment indicates that the static distributor and the fluid bed system had an increasing theoretical plate number (N) per meter of settled bed of solid phase support throughout the flow rate regimen investigated. It is further demonstrated that a flow rate above 5 cm/min is necessary in order to obtain a theoretical plate number of at least 100 N/m when the settled bed height of the adsorbent is 25 cm, while a flow rate above 10 cm/min is necessary in order to obtain a theoretical plate number of at least 100 N/m when the settled bed height of the adsorbent is 50 cm.

Example 5

Adsorption of Human IgG from Human Plasma

An expanded bed adsorption column (10 cm diameter) was y assembled as in Example 2 and containing a volume of adsorbent equal to a sedimented bed height of 50 cm. The adsorbent consisted of cross-linked agarose-tungsten carbide conglomerate beads, coupled with 4-amino-benzoic acid as the ligand, and having an average particle size (d (0.5)) by volume of 95 μm and a density of 2.9 g/ml (UpFront Chromatography A/S, Copenhagen, Denmark, product no.: CS118, batch 45818 WV). The adsorbent was suspended in a 25% glycerol solution in a potassium phosphate buffer pH 7.2. Just prior to use the column was washed with 30 bed volumes of deionised water.

The column was tested by the determination of the number of theoretical plates per meter (residence time distribution measurement, RTD) as described in example 1 at a linear flow rate of 10 cm/min and found to have 185 plates per meter settled bed (185 N/m)

The column was hereafter washed with 20 L of 0.1 M imidazole titrated with hydrochloric acid to pH 6.2 followed by 50 L of 0.002 M imidazole titrated with hydrochloric acid to pH 6.2 at a linear flow rate of 10 cm/min. The column was hereafter loaded with 40 L human plasma that was dialysed against 0.002 M imidazole/HCL pH 6.2 at a linear flow rate of cm/min. Following loading of the plasma the column was washed with 40 L imidazole/HCl at pH 6.2, whereafter the bound material remaining on the column was eluted by washing the column with 40 L 0.1 M potassium phosphate+0.5 M sodium chloride pH 7.5. The effluent from the column was monitored by a UV-monitor and the protein eluted from the column was collected according to the UV-signal. The bound and subsequently eluted protein was collected in an elution volume of 13 L. Following elution of the bound protein the column (still being connected to the inlet tubing and the outlet tubing) was dismantled from its stand and sealed by connection of the inlet tube and the outlet tubing in a closed loop, where after the entire column was disposed in an area designated biological waste material.

The unbound fraction running through the column, and the bound and subsequently eluted product, were analysed for protein content and it was found that more than 90% of the immunoglobulin G present in the normal human plasma pool was bound to the adsorbent and subsequently eluted in the potassium phosphate buffer. Other major protein fractions such as albumin did not bind to the adsorbent under these conditions.

During operation the column was observed by visual inspection and no channelling or un-wanted turbulence in the adsorbent was observed above approximately 10 cm from the bottom of the column. Close to the bottom some mixing and turbulence could be observed which was assigned to the designed effect of the distributor.

The invention claimed is:

1. A method of conducting upward flow expanded bed adsorption chromatography of a liquid comprising at least one component to be separated therefrom, comprising:
    supplying the liquid via an inlet to a stationary phase medium contained in a column, wherein the inlet is configured such that the liquid passes from the inlet to the bottom of the column, resulting in reduced turbulence and expansion of the stationary phase medium below a variable volume of headspace;
    allowing adsorption of the at least one component from the liquid by the stationary phase medium;
    withdrawing the liquid from the column via an outlet;
    regulating the expansion of the stationary phase medium by regulation of the flow rate of the liquid through at least the inlet; and
    restricting any overpressure in the headspace with respect to the pressure outside the column to be not more than said outside pressure plus 0.1 bar,
wherein
(A) the stationary phase medium comprises particles having (i) a density of at least 2.5 g/ml and (ii) a size of between 20 and 200 μm,
(B) a first pump provides a flow rate of the liquid in the column of at least 3 cm/min,
(C) the inlet is not a rotating inlet, and
(D) the inlet is not adapted for magnetically or mechanically driven stirring,
(E) the inlet comprises at least one tube comprising at least one horizontally or downwardly facing opening with a minimum size of at least 0.1 mm.

2. The method according to claim 1, wherein the overpressure is not more than 0.05 bar.

3. The method according to claim 1, wherein the overpressure is not more than 0.01 bar.

4. The method according to claim 1, wherein the first pump is upstream of the inlet for pumping said liquid into the column, and wherein the first pump regulates the expansion of the stationary phase medium.

5. The method according to claim 4, wherein the stationary phase medium comprises particles having a density of between 2.5 g/ml and 4.0 g/ml.

6. The method according to claim 4, wherein the theoretical plate number is at least 50 N/m.

7. The method according to claim 4, wherein the first pump provides a flow rate of said liquid in the column of at least 5 cm/min.

8. The method according to claim 4, wherein the first pump provides a flow rate of said liquid in the column of at least 7 cm/min.

9. The method according to claim 1, wherein the height of the liquid above the expanded stationary phase medium is regulated by a second pump downstream of the outlet for pumping said liquid out of the column.

10. The method according to claim 1, wherein the restriction of the overpressure is achieved by means of a vent.

11. The method according to claim 1, wherein the outlet comprises a pipe adapted such that an upstream end of the pipe may be moved to a selected position within the column, and the method further comprises the step of moving the upstream end of the pipe to a desired position in the column.

12. The method according to claim 1, comprising the further steps of:
    providing a stationary phase medium contained in a column having a lower portion comprising a sealed inlet and an upper portion comprising a sealed outlet and a sealed vent, all providing when unsealed a fluid connection between the interior and exterior of said column; and
    breaking the seals on the said inlet, outlet and vent before supplying the liquid to the stationary phase medium.

13. The method according to claim 12, comprising the further steps of, after allowing adsorption of the at least one component:
    eluting the at least one component from the stationary phase medium; and, after at least one iteration of the adsorption and elution steps,
    disposing of said column.

14. The method according to claim 13, wherein the maximum number of iterations of the adsorption and elution steps is 20.

15. The method according to claim 13, wherein the maximum number of iterations of the adsorption and elution steps is 15.

16. The method according to claim 13, wherein the maximum number of iterations of the adsorption and elution steps is 10.

17. The method according to claim 13, wherein the maximum number of iterations of the adsorption and elution steps is 5.

18. The method according to claim 13, wherein the disposal of the column is conducted without removing the stationary phase medium from the column.

19. The method according to claim 13, wherein, after the elution step, the stationary phase medium is cleaned and the column re-used.

20. The method according to claim 13, wherein, after elution of the at least one component from the stationary phase medium, and before disposal of the column, the method comprises the step of:

re-sealing the vent, outlet and inlet of the column.

21. A method of conducting expanded bed chromatography of a liquid comprising at least one component to be separated therefrom, comprising:

supplying the liquid via an inlet by means of at least a first pump upstream of the inlet to a stationary phase medium contained in a column, wherein the inlet is configured such that the liquid passes from the inlet to the bottom of the column, resulting in reduced turbulence and expansion of the stationary phase medium below a variable volume of headspace;

allowing adsorption of the at least one component from the liquid by the stationary phase medium; and withdrawing the liquid from the column via an outlet by means of at least a second pump downstream of the outlet, where (A) the stationary phase medium comprises particles having (i) a density of at least 2.5 g/ml and (ii) a size of between 20 and 200 μm, (B) a first pump provides a flow rate of the liquid in the column of at least 3 cm/min, (C) the inlet is not a rotating inlet, and (D) the inlet is not adapted for magnetically or mechanically driven stirring, and (E) the inlet comprises at least one tube comprising at least one horizontally or downwardly facing opening with a minimum size of at least 0.1 mm.

* * * * *